United States Patent
Shetty et al.

(10) Patent No.: US 9,592,343 B2
(45) Date of Patent: *Mar. 14, 2017

(54) SYRINGES FOR REPETITIVE MIXING AND DELIVERY OF INJECTABLES

(71) Applicant: UNITRACT SYRINGE PTY LTD, Sydney (AU)

(72) Inventors: Gautam N. Shetty, Lancaster, PA (US); Lou Castagna, Middletown, PA (US)

(73) Assignee: Unitract Syringe Pty Ltd., Sydney (AU)

( * ) Notice: Subject to any disclaimer, the term of this patent is extended or adjusted under 35 U.S.C. 154(b) by 215 days.

This patent is subject to a terminal disclaimer.

(21) Appl. No.: 14/333,451

(22) Filed: Jul. 16, 2014

(65) Prior Publication Data
US 2015/0025455 A1    Jan. 22, 2015

Related U.S. Application Data

(60) Provisional application No. 61/846,940, filed on Jul. 16, 2013, provisional application No. 61/941,862, filed on Feb. 19, 2014.

(51) Int. Cl.
*A61M 5/24* (2006.01)
*A61M 5/315* (2006.01)
(Continued)

(52) U.S. Cl.
CPC ...... *A61M 5/2448* (2013.01); *A61M 5/31525* (2013.01); *A61M 5/31535* (2013.01);
(Continued)

(58) Field of Classification Search
CPC ............ A61M 5/2448; A61M 5/31591; A61M 5/31596; A61M 2005/2451; A61M 2005/31598
See application file for complete search history.

(56) References Cited

U.S. PATENT DOCUMENTS

| | | | | |
|---|---|---|---|---|
| 5,785,683 A | * | 7/1998 | Szapiro | A61M 5/284 604/228 |
| 5,865,798 A | * | 2/1999 | Grimard | A61M 5/31596 604/218 |

(Continued)

FOREIGN PATENT DOCUMENTS

| | | | |
|---|---|---|---|
| DE | 1815118 A1 | * | 6/1970 |
| DE | 1815118 A1 | | 6/1970 |

(Continued)

OTHER PUBLICATIONS

Wetzel et al, U.S. Appl. No. 14/333,442, filed Jul. 16, 2014, entitled, "Syringes for Prefilled and Fill-at-Use Mixing and Drug Delivery."

(Continued)

*Primary Examiner* — Andrew Gilbert
(74) *Attorney, Agent, or Firm* — Wiley Rein LLP

(57) ABSTRACT

Mixing syringes including a valve mechanism are configured and configurable to enable one or more substances to be prefilled into the syringe. The valve mechanism may be an aspect of a distal seal assembly. Actuation of the valve mechanism permits opening of a fluid passage for the mixing of one or more substances, and the resulting mixed substance can be delivered by the syringe, for example, for administration of a pharmaceutical to a subject. The repetitive mixing of substances contained in a distal and proximal chamber is also provided, where the plunger rod is configured to releasably engage a locking mechanism to actuate the valve, and can axially displace the distal seal assembly while the fluid passage is open.

13 Claims, 24 Drawing Sheets

(51) Int. Cl.
*A61M 5/32* (2006.01)
*A61M 5/31* (2006.01)

(52) U.S. Cl.
CPC .... *A61M 5/31578* (2013.01); *A61M 5/31591* (2013.01); *A61M 5/31596* (2013.01); *A61M 5/322* (2013.01); *A61M 5/3234* (2013.01); *A61M 2005/2451* (2013.01); *A61M 2005/3128* (2013.01)

(56) References Cited

U.S. PATENT DOCUMENTS

| | | | |
|---|---|---|---|
| 5,891,087 A | 4/1999 | Ohtani et al. | |
| 6,149,628 A * | 11/2000 | Szapiro | A61M 5/31596 604/191 |
| 6,602,223 B2 | 8/2003 | Szapiro et al. | |
| 7,048,720 B1 * | 5/2006 | Thorne, Jr. | A61M 5/284 604/191 |
| 7,101,354 B2 | 9/2006 | Thorne, Jr. et al. | |
| 7,951,108 B2 | 5/2011 | Harper et al. | |
| 7,998,106 B2 | 8/2011 | Thorne, Jr. et al. | |
| 8,002,734 B2 | 8/2011 | Bassarab et al. | |
| 8,096,971 B2 | 1/2012 | Bassarab et al. | |
| 8,556,848 B2 * | 10/2013 | Klug | A61M 5/31596 604/89 |
| 8,679,056 B1 * | 3/2014 | Wu | A61M 5/31596 604/89 |
| 8,992,505 B2 * | 3/2015 | Thorne, Jr. | A61M 5/31596 604/122 |
| 2004/0138611 A1 * | 7/2004 | Griffiths | A61M 5/2033 604/82 |
| 2004/0186432 A1 * | 9/2004 | Barry | A61M 5/30 604/152 |
| 2007/0185438 A1 * | 8/2007 | Haimi | A61M 5/31596 604/82 |
| 2009/0018496 A1 * | 1/2009 | Harper | A61M 5/31596 604/89 |
| 2010/0106086 A1 * | 4/2010 | Sudo | A61M 5/284 604/83 |
| 2012/0136298 A1 * | 5/2012 | Bendix | A61M 5/2448 604/89 |
| 2012/0265171 A1 * | 10/2012 | Thorne, Jr. | A61M 5/31596 604/518 |
| 2013/0060203 A1 * | 3/2013 | Svensson | A61M 5/31596 604/222 |
| 2013/0165853 A1 | 6/2013 | Kawamura | |

FOREIGN PATENT DOCUMENTS

| | | |
|---|---|---|
| EP | 0242956 A1 | 10/1987 |
| EP | 1520597 A1 | 4/2005 |
| EP | 1758685 B1 | 11/2011 |
| GB | 1214053 A | 12/1970 |
| WO | 99/17820 A1 | 4/1999 |
| WO | 99/20562 A1 | 4/1999 |
| WO | 2010/144021 A1 | 12/2010 |

OTHER PUBLICATIONS

Shetty et al., U.S. Appl. No. 14/333,465, filed Jul. 16, 2014, entitled, "Syringes for Sequential Delivery of Injectables."
International Search Report and Written Opinion, mailed Nov. 6, 2014, cited in related International Patent Application No. PCT/US2014/046912, filed Jul. 16, 2014.

* cited by examiner

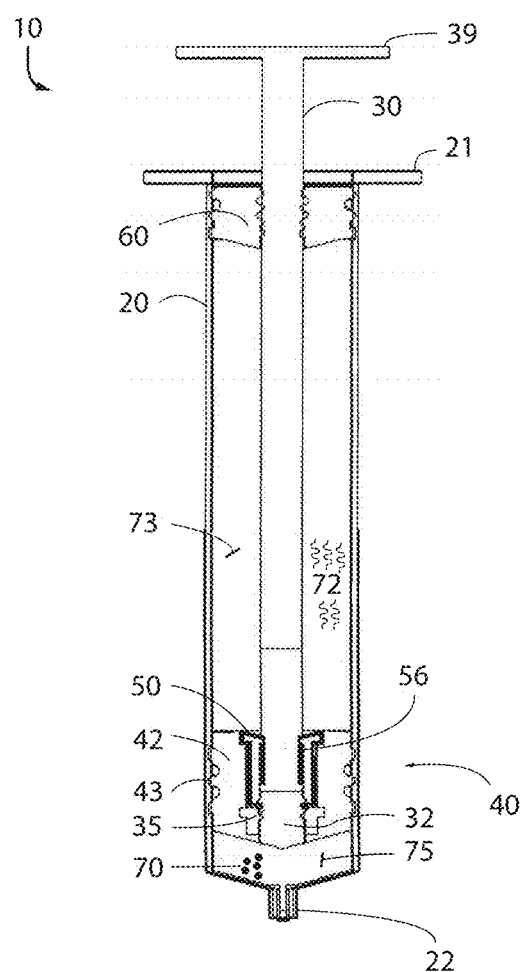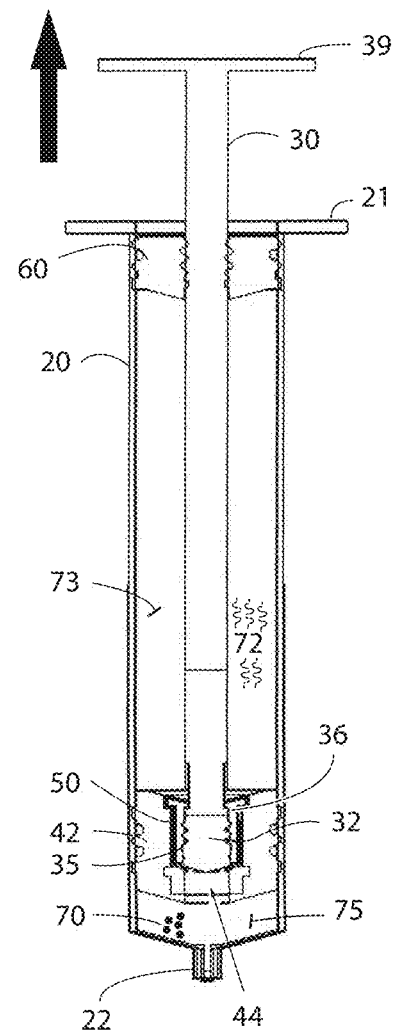
FIG. 1A
FIG. 1B

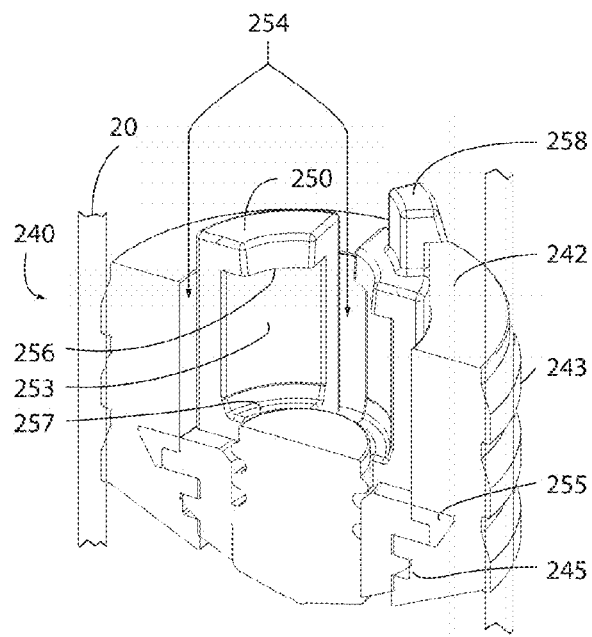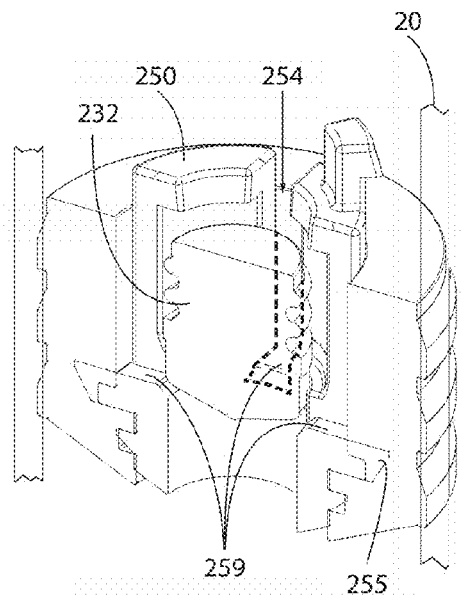
FIG. 6A   FIG. 6B
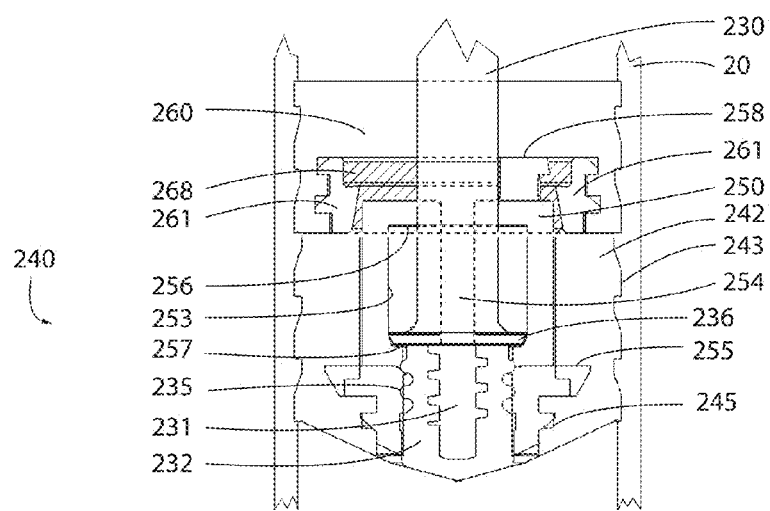
FIG. 6C

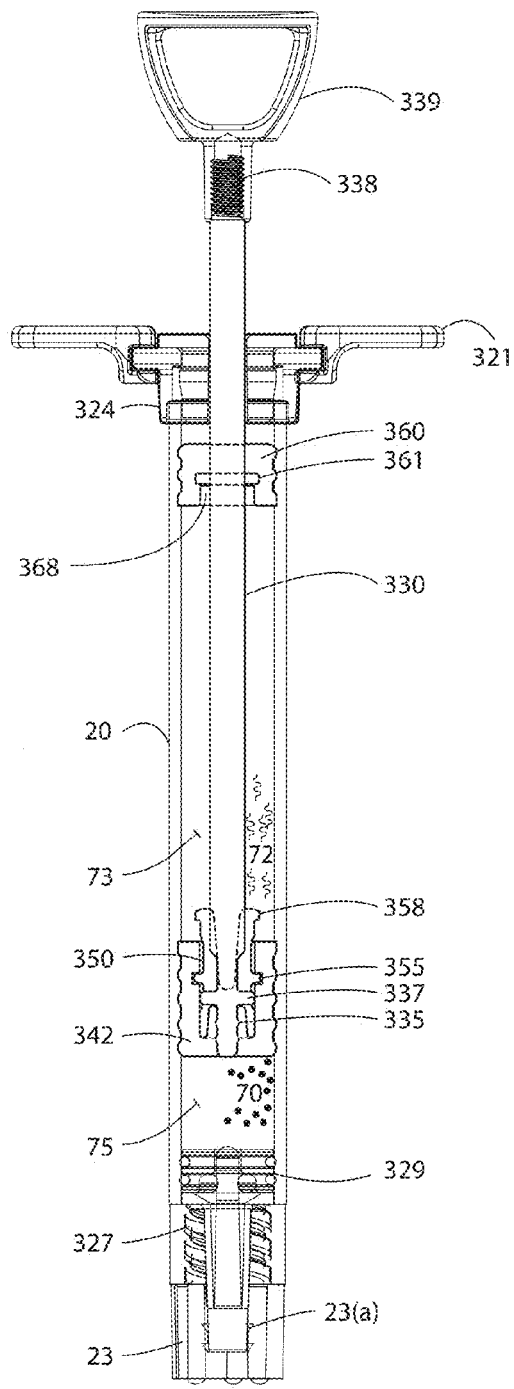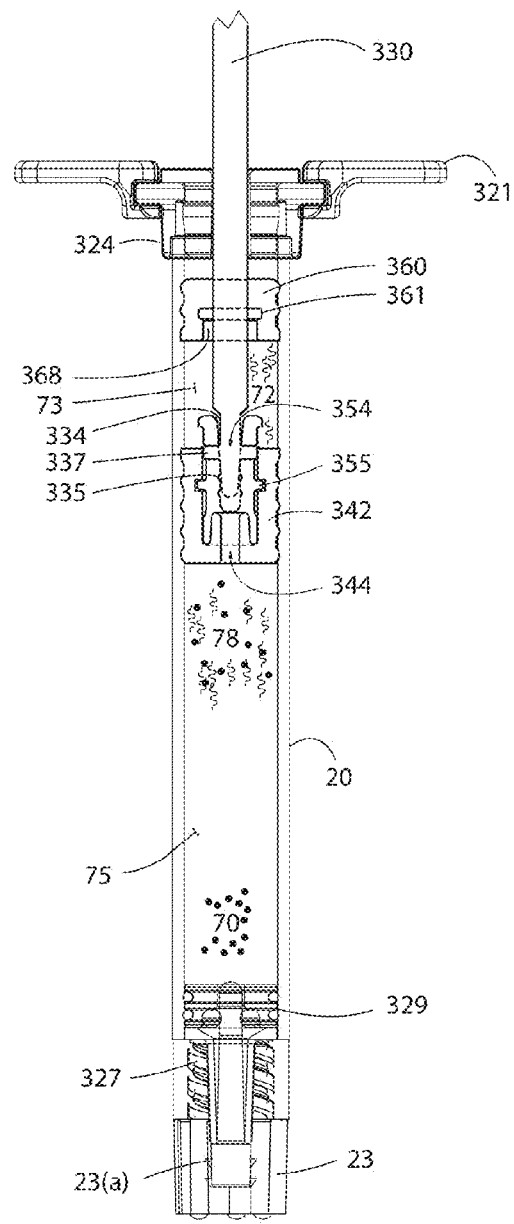
FIG. 8A
FIG. 8B

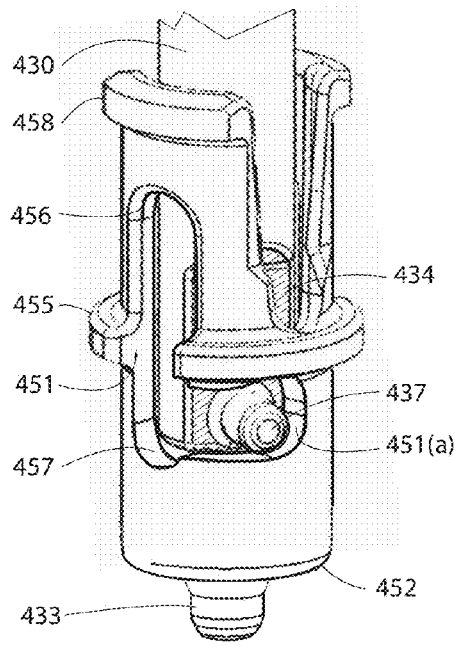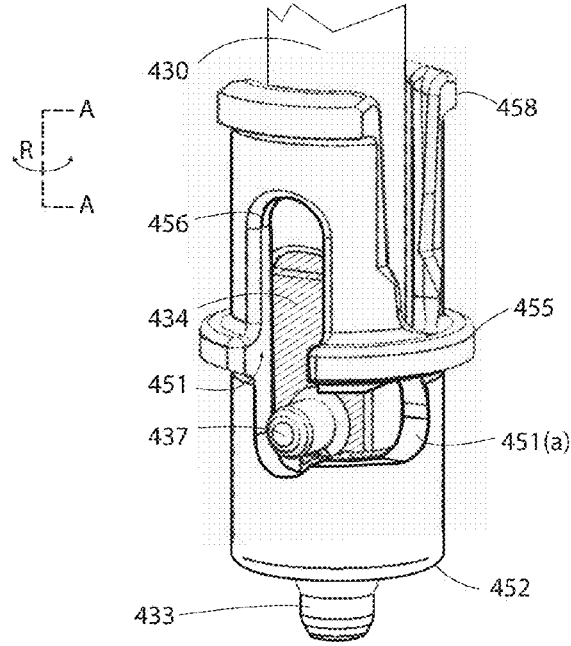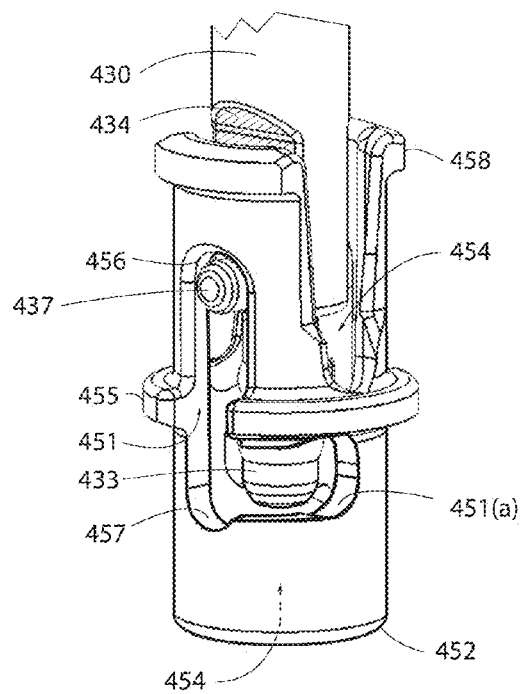

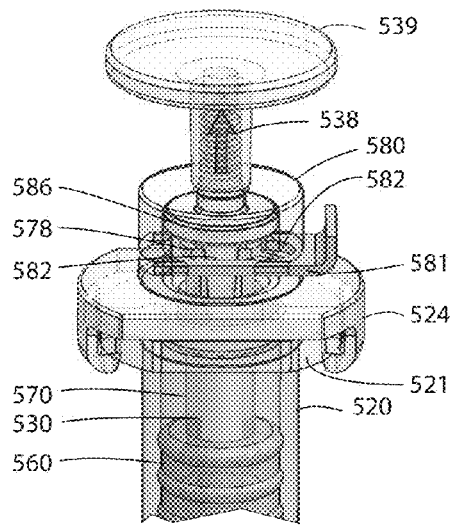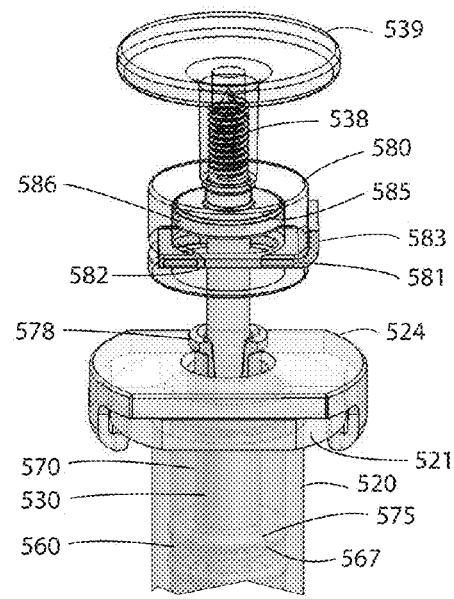
FIG. 12A    FIG. 12B
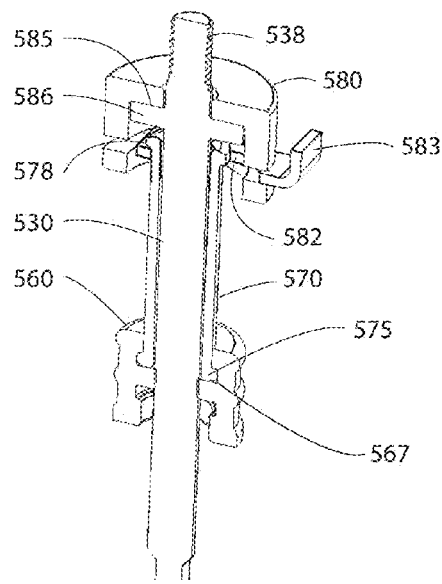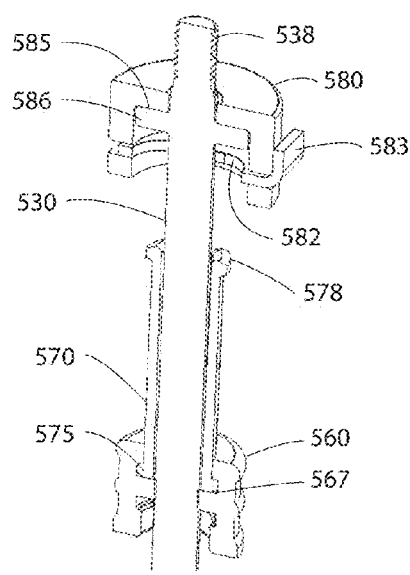
FIG. 12C    FIG. 12D

SYRINGES FOR REPETITIVE MIXING AND DELIVERY OF INJECTABLES

RELATED APPLICATIONS

This application claims priority benefit of U.S. Patent Applications No. 61/846,940, filed 16 Jul. 2013, and No. 61/941,862, filed 19 Feb. 2014, the contents of which are incorporated fully herein by reference for all purposes.

FIELD

The embodiments described herein relate to mixing syringes. More specifically, these embodiments relate to syringes configured and configurable to enable at least one substance to be prefilled into the syringe, or at least one substance to be filled at time-of-use by the end-user without mixing with the prefilled substance. The resulting arrangement enables syringes that are capable of storing, mixing, and delivering of one or more substances, such as pharmaceutical substances.

BACKGROUND

The number of drugs supplied in lyophilized or powdered form has been growing at an increased rate over the past several years, reflecting the increase in the introduction of biological drugs. For example, because of stability and shelf life factors, therapeutic proteins are often formulated as powders that must be reconstituted prior to injection. A growing number of drugs and biologics supplied in powder form are including reconstitution vial systems that incorporate a vial adapter or vial transfer device. Dual chamber drug cartridges and syringes go a step further and allow reconstitution to take place within the device immediately prior to injection. This allows, for example, a diluent to be added to a dehydrated, lyophilized, desiccated or powdered active substance immediately prior to injection, which is particularly useful for substances that are subject to degradation or loss of activity when stored in a liquid form.

The majority of mixing devices for syringes utilize sequential chambers, wherein the syringe has one barrel having a proximal chamber and a distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

Some other mixing syringes utilize concentric barrel configurations. Many concentric barrel mixing syringes to date, however, require complex assemblies, multiple operation steps by the user, or other particular nuances that make them difficult to manufacture, assemble, or operate. For example, some existing concentric barrel mixing syringes require concentric inner and outer barrels that are selectively rotatable with respect to each other, and require one or more sealing rings that contain a passage means therein. The barrels must be rotated to align a hole in the inner barrel with the passage means in a sealing ring. Such configurations require complex components and cumbersome requirements for the user to operate the device. Other concentric barrel designs utilize outer and inner telescopic tubular elements seated inside a barrel and coaxial with the longitudinal axis. The outer tubular element and barrel form a chamber which holds a reservoir of liquid. The inner tubular element has an end nearby the injection port with a seal thereon that has an orifice therein. Accordingly, such mixing syringe configurations require three tubular elements, with the outer and inner concentric chambers residing inside a third barrel. Still other dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. As with other mixing devices comprising concentric barrels, these are also complicated in structure and often require rotation of the barrels to align one or more apertures that enable a flow of a liquid substance from one chamber into another.

Thus, there are complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among other factors. As such, various sterility, sealing and venting arrangements have been used which have limitations in terms of ease of manufacture and operation of the mixing device. Given the complexities of current drug substances, particularly related to sensitive biologics, there remains a need for mixing syringes that provide ease in manufacture, maintenance, and handling. There is also a need for mixing syringes that provide for repetitive mixing in preparation for intended use.

SUMMARY

The embodiments of the present invention provide for mixing syringes that alleviate one or more of the problems associated with existing mixing syringes. For example, the embodiments provide for prefillable repetitive mixing syringes for maintaining, mixing, and administering substances, for example a labile pharmaceutical agent, such as a biologic.

At least one embodiment provides for a prefillable repetitive mixing syringe comprising a syringe housing; a distal seal assembly axially displaceably disposed within the housing, wherein the position of the distal seal assembly defines a mutable distal chamber and a mutable proximal chamber within the housing; the distal seal assembly further comprising a valve that regulates a fluid passage between the proximal and distal chambers; a plunger rod positioned coaxially within the syringe housing and engaged with the distal seal assembly, wherein the plunger rod is configured to releasably engage a locking mechanism to actuate the valve, and whereby the plunger rod can axially displace the distal seal assembly while the fluid passage is open. In an aspect of the embodiment, the prefillable repetitive mixing syringe further includes a proximal seal. The proximal seal or distal seal assembly can further include a connector to irreversibly connect together the distal and proximal seals. In a further aspect of the embodiments, the locking mechanism comprises a radial channel configured to be rotatably engaged by a plunger rod protrusion.

In at least one embodiment, the prefillable repetitive mixing syringe further comprises an insert housed at least partially within the distal seal assembly, wherein the insert comprises an internal cavity configured to engage the distal end of the plunger rod. The insert may include at least one channel or compartment that regulates movement of the plunger rod within the insert, and wherein the insert comprises at least one fluid passage. The insert may also include a connector to engage with the proximal seal. The insert may also include a radial channel configured to be rotatably engaged by a plunger rod protrusion.

In some embodiments, the distal chamber, proximal chamber, or both, contains a substance. The substance may be a diluent. The substance may be lyophilized. The substance may comprise a pharmaceutical agent. The pharmaceutical agent may be a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, or a combination of any of these. The pharmaceutical agent may be lyophilized In yet another aspect, the embodiments provide for methods of assembling the mixing syringes described herein. In a still further aspect, the embodiments provide for methods of operating the syringes.

In at least one embodiment, the mixing syringe further comprises a dose control mechanism.

In at least one embodiment, the mixing syringe is further configured as a safety syringe having a retractable needle.

In another aspect of the embodiments, the mixing syringe further comprises a luer-type connection or luer adapter positioned within or at the distal end of the syringe housing.

Additionally, the mixing device may facilitate the storage of multiple component pharmaceutical substances in the proximal and distal chambers, thereby maintaining the stability and efficacy of the pharmaceutical substances during transport and over prolonged periods of storage. In a particular embodiment of the invention, the syringe is a prefilled syringe.

BRIEF DESCRIPTION OF THE DRAWINGS

Non-limiting embodiments of the invention are described herein with reference to the drawings.

FIG. 1A to FIG. 1E present a series of cross-sectional views, each showing positions of components and parts of an embodiment as they appear in various stages of use of the embodiment.

FIG. 6A-to FIG. 6C present detailed views of an embodiment of a distal seal assembly.

FIG. 8A to FIG. 8D show cross-sectional views of an embodiment of the mixing syringe of the invention in several stages of use.

FIG. 10A to FIG. 10C depict an embodiment of a valve mechanism configured with a locking aspect, in the locked position for aspiration (FIG. 10A), unlocked position (FIG. 10B), and opened position (FIG. 10C).

FIG. 12A to FIG. 12D present exploded views of an embodiment of a syringe in which a locking aspect comprising the proximal valve and plunger rod configuration allows the mutable distal chamber to be filled and emptied independent of the prefilled mutable proximal chamber.

DETAILED DESCRIPTION

Figures 1C, 1D, 1E:
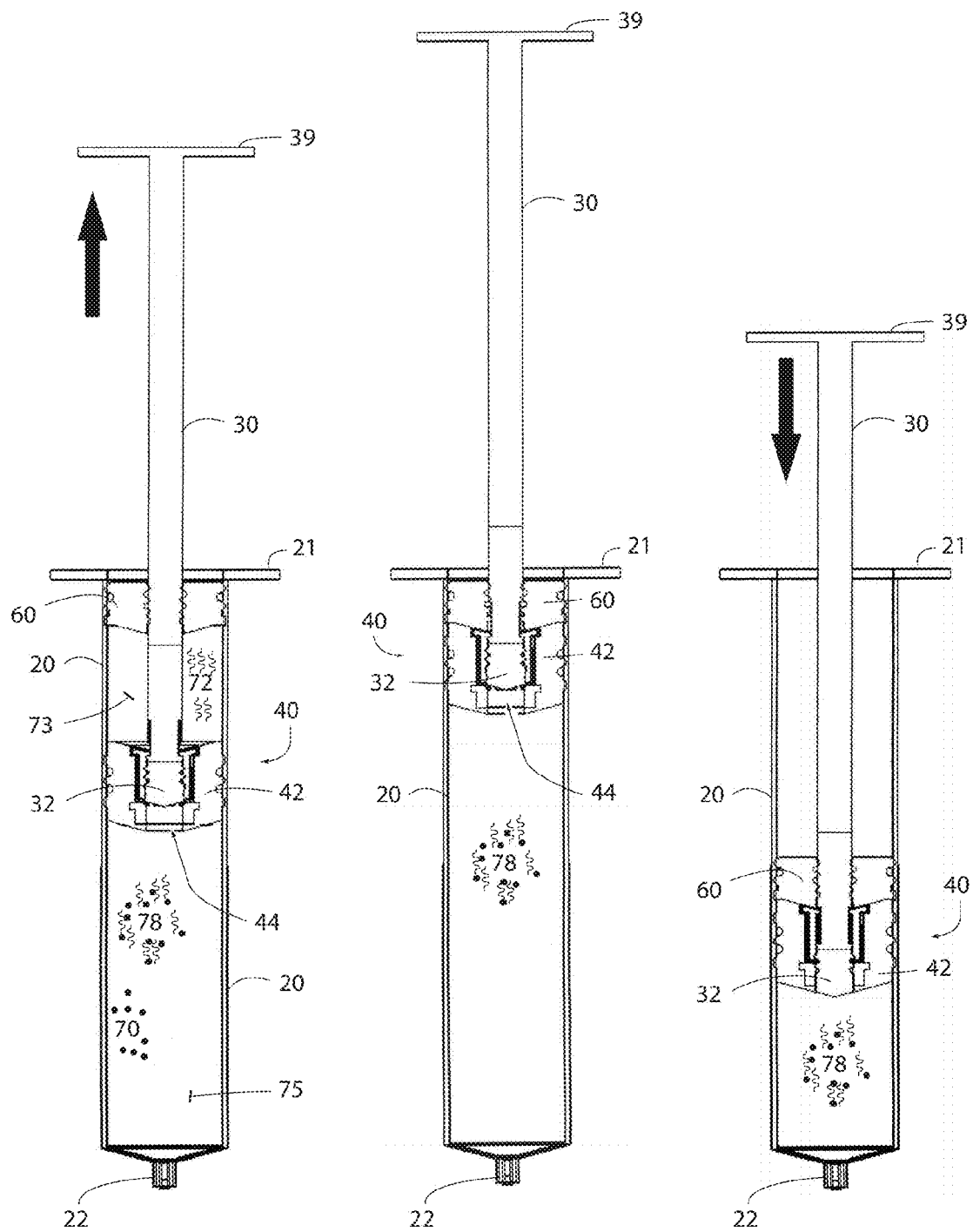

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

The present embodiments provide for mixing syringes which generally comprise at least a first chamber for containing a first substance and a second chamber for containing a second substance, such that seals within the syringe are configured for maintaining the substances separately in their respective chambers until such time as it is desired by a user to mix the components within the syringe by manipulating the seals to provide fluid communication between the chambers.

References to "prefillable" generally refer to syringes comprising components for filling with a substance prior to dispensing the substance for its intended use. More specifically, in the context of the mixing syringe embodiments, the term "prefillable" refers to a configuration or state in which a substance may be introduced into the syringe any time prior to the dispensing by the syringe of the substance(s) for their intended use (such as delivery into a subject or device either directly or indirectly). A prefillable mixing syringe thus includes syringes described herein as prefilled, fill-at-time-of-use, fill-on-demand, ready-to-use, and the like.

References to "pharmaceutical agent," "pharmaceutically active," "pharmaceutical," "drug," "medicament" "active agent," "active drug" and the like, refer in a general sense to substances useful in the medical and scientific arts as suitable for delivery via a syringe, including, for example, drugs, biologics, diagnostic agents (e.g, dyes or contrast agents) or other substances used for therapeutic, diagnostic, or preventative (e.g., vaccines), or research purposes. Example pharmaceutical agents include biologics, vaccines, chemotherapeutic agents, contrast agents, small molecules, immunogens, antigens, interferons, polyclonal antibody preparations, monoclonal antibodies, anesthetics, interfering RNAs, gene vectors, insulins, or combinations of any of these. "Inactive" substances refer to carriers, excipients, diluents, and the like, which are well-known in the art, although such substances may have beneficial function in the mixed injectable, such as, for example, adjuvants, isotonic or buffering agents. These active or inactive substances may also include substances having immediate, delayed or sustained release characteristics.

"Fluid" refers primarily to liquids, but can also include suspensions of solids dispersed in liquids (dispersions, suspensions, colloidal mixtures), emulsions, liposomal compositions, and gasses dissolved in or otherwise present together within liquids inside the fluid-containing portions of syringes.

As used herein to describe the relative positions of the components of the present embodiments, the terms "axial" or "axially" refer generally to a longitudinal axis "A" of the barrel of the syringe and plunger in which or around components are positioned, although not necessarily symmetrically there-around. The term "radial" refers generally to a direction perpendicular to axis A. The terms "proximal," "rear," "rearward," "back," or "backward" refer generally to an axial direction in the direction "P." The terms "distal," "front," "frontward," "depressed," or "forward" refer generally to an axial direction in the direction "D," toward the dispensing end of the syringe.

As used herein, the term "glass" should be understood to include other similarly non-reactive materials suitable for use in a pharmaceutical grade application that would normally require glass (e.g., Type I borosilicate glass), including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, or plasticizers, etc., and that can be formed or molded under heat and pressure. As used herein, the term "plastic" can include pharmaceutical grade non-reactive polymers or elastomers that are approved for use in applications where they are in direct contact with therapeutic substances, such that the plastics do not interact with the substances contacting the plastic and are not readily susceptible to leaching or gas migration under ambient temperature and pressure.

The term "elastomer," "elastomeric" or "elastomeric material" refers primarily to cross-linked thermosetting rubbery polymers that are more easily deformable than resilient plastics, are approved for use with pharmaceutical grade substances, and are not readily susceptible to leaching or gas migration under ambient temperature and pressure.

The present embodiments provide for mixing syringes in which a distal seal assembly maintains substances in separate, mutable chambers until a user displaces a plug seal within the distal seal assembly, opening a passage within the distal seal assembly and allowing the separated substances to mix within the syringe. Prefilled mixing syringes are advantageous in avoiding confusion whether a vial is multidose or single dose, or confusion regarding which diluent should be used with a given lyophilized or powder medicament. Additional embodiments provide for syringes in which one mutable chamber is configured to be prefilled, and another mutable chamber is configured to be loaded at or near the time-of-use.

In one aspect, the embodiments provide for a mixing syringe having a syringe housing with a proximal end and a distal end, and a mutable proximal chamber and a mutable distal chamber defined within the syringe housing. The syringe includes a plunger rod configured to translate substantially axially within the barrel of the housing and between the proximal end and distal end of the housing to deliver one or more substances. The distal end of the housing may be configured to connect to, or be connected to, a needle, cannula, or other conduit for fluid transfer from the mixing syringe to a subject, patient, intravenous (i.v.) line, fluid tube, container, scientific instrument, or the like. In at least one embodiment, the distal end of the housing has a luer type connection, such as a luer lock connection, for connection of the barrel to a vial, container, needle, or i.v. line. The syringe further includes a distal seal assembly, and at least a portion of distal end of the plunger rod may be engaged with the distal seal assembly. The distal seal assembly may comprise a valve-type seal, wherein a portion of the seal assembly may move with reference to the remainder of the seal assembly to open and close one or more passages within the distal seal assembly, thus permitting an operator to effect fluid communication between the mutable distal chamber and the mutable proximal chamber. The mutable chambers are defined by the position of the distal seal assembly within the housing, and by the distal or proximal interior walls of the housing, by suitable seals located within the housing, or by a proximal seal assembly that can be configured to engage with the distal seal assembly. In at least one embodiment, the valve-type seal of the distal seal assembly has an inner plug seal oriented axially within an outer ring seal, such that a passage is closed when the plug seal and ring seal are in a first position, and the passage is opened when the plug seal is moved into a second position at least partially apart from the ring seal. The plug seal may be attached to or be an aspect of (e.g., a region of) the distal end of the plunger rod. The distal seal assembly may optionally include a locking aspect capable of locking the valve-type seal. The distal seal assembly may comprise an insert that provides at least part of the structure of the valve-type mechanism or locking aspect.

The distal seal may optionally have a connector that facilitates connection between the distal seal assembly and the proximal seal once the distal seal has been proximally translated to meet the proximal seal. Alternatively, the distal seal and the proximal seal may be connected or held in connection by a vacuum created there-between or pressure from the chamber containing the mixed substances, with or without the use of such an optional connector/connection feature. In these embodiments, when the distal seal engages the proximal seal by connection (e.g., via a connector) or physical forces within the syringe (e.g., vacuum), the proximal seal and the distal seal may translate axially within the barrel as if a unified component. In at least one embodiment, the proximal seal is retained in a substantially fixed position within the housing until connection with the distal seal. Accordingly, once the distal and proximal substances have been mixed, translation of the plunger rod in the distal direction can translate both the proximal and distal seals in the distal direction to force the mixed substance from the distal end of the housing.

In at least some embodiments, the mutable proximal chamber and the mutable distal chamber may contain one or more mixing substances, i.e., first and second mixing substances (or distal and proximal substances), which substances may each be a powder, crystal, solid, fluid, liquid, suspension, gas, or other substances suitable for mixing. One of more of the substances can be pharmaceutically active. The substance in the mutable proximal chamber and the mutable distal chamber may be prefilled or filled on-demand, such as near or at the time of use.

In at least one embodiment, as the operator translates the plunger rod in the proximal direction, the plug seal is (optionally, temporarily) moved into a second position partially apart from the distal seal assembly, e.g., apart from the distal ring seal or an insert therein, such that the passage is opened. As the operator withdraws the plunger rod, the passage may remain open for the transfer of substances between portions of the barrel that are proximal and distal (or vice versa) through the distal seal assembly. In this way, the distal seal assembly defines mutable proximal and distal chambers within the barrel, and facilitates the movement of substances between the mutable proximal and distal chambers.

In at least one embodiment, the mixing of the substances is facilitated by creating a pressure differential between the mutable proximal chamber and the mutable distal chamber.

In one or more embodiments, the syringe may be configured to enable a prefilled arrangement or a fill-at-time-of-use arrangement. For example, during the manufacturing process at least one of the chambers of the mixing syringe may be prefilled with one or more mixing substances. Alternatively, one or more chambers may be prefilled, while one or more other chambers are configured to be filled on-demand, e.g., filled just prior to use. For example, in at least one embodiment, the mutable proximal chamber of the mixing syringe comprises a proximal substance, and the mutable distal chamber is configured to be filled on-demand prior to use, or at the time use, by an end-user, for instance a physician, pharmacist, nurse, caregiver, patient, or the like. In another alternative, both chambers may be configured to be filled on-demand, e.g., filled just prior to use. In this embodiment, the syringe can be oriented so that gravity assists the loading of a substance into the proximal chamber (P) via the distal chamber (D). The distal chamber may then be loaded with the same or a different substance (including differing concentrations, potencies, formulations and the like, of the same substance). Such arrangements may be facilitated by the use of one or more locking mechanisms that function to enable the valve-type seal to remain closed during some stages of operation (such as for filling), but permit the valve-type seal to open a fluid passage there-through during other stages of operation (such as for mixing). In at least one embodiment, the mixing syringe comprises a locking mechanism that allows for sequential delivery of substances with or without mixing or repetitive mixing of the substances.

In some embodiments, the proximal and distal chambers can be prefilled to contain one or more mixing substances, i.e., proximal and distal mixing substances, which may each be a powder, solid, liquid, suspension, gas, or mixtures of these substances. For example, the distal mixing substance locatable in the distal chamber may be a fluid that comprises a pharmaceutically active fluid or a pharmaceutically inactive fluid, such as a diluent. The proximal mixing substance locatable in the proximal chamber may be a fluid that comprises a pharmaceutically active fluid or a pharmaceutically inactive fluid, such as a diluent. Alternatively, for example, the proximal substance locatable in the proximal chamber may comprise a pharmaceutically active solid or an inactive solid excipient, and the distal substance may comprise a pharmaceutically active fluid or a pharmaceutically inactive fluid; or the proximal substance in the proximal chamber may comprise a pharmaceutically active fluid or a pharmaceutically inactive fluid, and the distal substance may comprise a pharmaceutically active solid or an inactive solid excipient. As is well understood in the art, a pharmaceutically active component may be mixed with suitable excipients in its respective mutable chamber in the prefilled syringe. For example, a powdered drug is often lyophilized with salts, sugars, or polyols, such as mannitol or lactose; a liquid drug is often formulated in ethanol, buffers, or non-aqueous or aqueous solvents.

In one embodiment, for example, a first mixing substance locatable in the mutable distal chamber may be fluid, and a second mixing substance locatable in the mutable proximal chamber may also be a fluid. One or both of the fluids may be pharmaceutically active. Alternatively, for example, the first mixing substance locatable in the mutable distal chamber (a distal substance), may be a solid. The solid may be a pharmaceutically active solid, such as a biologic, drug or dye, or a pharmaceutically inactive solid such as an excipient. The second mixing substance locatable in the mutable proximal chamber (a proximal substance), may be, for example, a fluid. The fluid may be a pharmaceutically active fluid, such as a biologic, drug or dye, or a pharmaceutically inactive fluid, such as a diluent. Alternatively, the first substance locatable in the distal chamber may be a fluid, and the second mixing substance, locatable in the proximal chamber, may be a solid. When the mutable distal chamber is filled with a fluid, the chamber may be prefilled or filled on-demand, such as near or at the time of use.

In one embodiment, the mutable distal chamber contains a pharmaceutically active solid and the mutable proximal chamber contains a pharmaceutically inactive liquid diluent, such as water for injection, whereby entry of the diluent through the passage of the distal seal assembly, once opened, facilitates mixing of the diluent with the pharmaceutically active solid. The mixing of the diluent and the pharmaceutically active solid enables reconstitution of the pharmaceutically active solid for, as an example, subsequent delivery of pharmaceutically active compound to a patient.

In another embodiment, the mutable distal chamber contains a pharmaceutically active solid and the mutable proximal chamber contains a pharmaceutically active fluid, whereby entry of the fluid through the passage in the distal seal assembly, once opened, facilitates mixing with the pharmaceutically active solid in the distal chamber. The mixing of the pharmaceutically active fluid and the pharmaceutically active solid enables reconstitution of the pharmaceutically active solid for, e.g., subsequent delivery of both pharmaceutically active compounds to a patient.

In yet another embodiment, the distal chamber contains a first pharmaceutically active fluid and the proximal chamber contains a second pharmaceutically active fluid, whereby entry of the first pharmaceutically active fluid through the passage facilitates mixing with the second pharmaceutically active fluid in the distal chamber. The mixing of the first pharmaceutically active fluid and the second pharmaceutically active fluid enables mixing of the pharmaceutically active fluids, e.g., for subsequent delivery of both pharmaceutically active compounds to a patient.

In another embodiment, at least one of the chambers of a mixing syringe may be filled just prior to use, such as by the physician, pharmacist, nurse, caregiver, patient, end-user, or the like. Similarly, one or more chambers may be pre-filled, while one or more other chambers are filled just prior to use. Such an arrangement may be facilitated by the use of one or more locking mechanisms. The locking mechanisms function to enable the valve-type seal to remain closed during some stages of operation (such as for filling), but permit the valve-type seal to open a fluid passage therethrough during other stages of operation (such as for mixing or for dispensing an unmixed fluid from the proximal chamber). For example, a locking mechanism may be configured in the valve mechanism/assembly. Alternatively, a locking mechanism can be configured apart from the valve mechanism, such as in a plunger/proximal seal latch/release system. When the locking feature is engaged, and the distal chamber loaded, the distal substance can be expelled without mixing. When the locking feature is disabled, the device operates much the same way as the above embodiments (i.e., withdrawing the plunger rod in the proximal direction opens the fluid path to allow mixing). After the distal chamber is filled, the syringe is ready for the mixing feature, and the plunger rod may be further translated in the axial direction to open the fluid passage within the distal seal for mixing substances. The plunger rod becomes disengaged from the proximal seal to allow for this mixing to occur. Thereafter, the plunger rod can be translated axially in the distal direction for drug delivery. Additionally, when the locking feature (of the distal or proximal seals) are maintained in the closed/locked position, the syringe can be used to load and deliver fluid from the distal chamber independent of the proximal chamber and without mixing with the proximal chamber, allowing for sequential delivery of fluids (e.g., unmixed, then mixed; or a first fluid from the distal chamber, then a second fluid from the proximal chamber) from the same syringe.

Another embodiment provides for a valve mechanism that allows for partial and repeated mixing steps within the same mixing syringe. In a particular embodiment, an intermediate open/closed position in the valve allows for repeated proximal/distal translation of the plunger which successively mixes proximal and distal substances until the mutable proximal chamber is collapsed and any remainder of proximal substance is mixed with the distal substance. This feature allows the relative concentrations of the distal and proximal substances to be uniform as the proximal and distal substances are mixed and the mixed substances are expelled from the mixing syringe. This feature also allows the relative concentrations of the distal and proximal substances to vary (e.g., from more concentrated distal substance relative to proximal substance, to less concentrated distal substance relative to proximal substance) as the proximal and distal substances are mixed and the mixed substances are expelled from the mixing syringe. An additional feature employs a locking mechanism that allows optional independent loading and delivery from the mutable distal chamber before employing the mixing feature of the syringe.

An additional aspect of the present invention provides for mixing syringes further capable of connecting to selectable needle assemblies, or to a needleless access device such as an i.v. line. Particular embodiments of such devices are described in U.S. Patent Applications No. 61/934,963, filed 3 Feb. 2014; No. 61/898,077, filed 31 Oct. 2014; and No. 61/863,098, filed 7 Aug. 2013, each of which is incorporated fully herein for all purposes. The connection aspect may be pre-formed as a distal portion of the syringe barrel housing. Alternatively, the syringe barrel may be a substantially straight barrel to which a connection adapter is mounted. An adapter mountable to a syringe barrel may have a luer connection portion and a barrel-engaging portion and a fluid aperture therethrough. The adapter facilitates mounting a luer assembly to the barrel. The luer assembly may be a tip cap having a corresponding female luer fitment for connection to the male luer fitment of the luer connection portion of the adapter. The luer assembly may alternatively be a luer needle assembly having a needle body, cannula, and a needle tip having a corresponding female luer fitment for connection to the male luer fitment of the luer connection portion of the adapter. The adapter and syringe may further comprise an immobile, compressible needle seal, which is adjacent to or engageable with the barrel-engaging portion of the adapter. For example, a needle seal sits within the interior of the barrel or adapter, and has a fluid pass-through axially located for the passage of fluid.

In at least one embodiment, the syringe is a retractable syringe that comprises a retractable needle.

In at least one embodiment, the plunger may be a conventional plunger. In another embodiment, the plunger is an accurate dose delivery plunger.

The present embodiments are particularly useful for the administration of lyophilized pharmaceuticals, including small molecules and biologicals, such as those presently marketed as lyophilized or powdered drugs for injection. These include, by way of non-limiting examples, ActHIB® vaccine, Aldesleukin, ampicillin, asparaginase, amphotericin B (Amphotec, Amphocin, others), ATryn antithrombin, Bendamustine, Bleomycin, Bortezomib, Carboplatin, Carmustine, Caverject Powder (Alprostadil), Certolizumab (CIMZIA®), Cefazolin, Cefonicid, Ceftazidime, Ceftriaxone sodium, Cisplatin, Cytarabine, Cytoxan (cyclophosphamide), Dacarbazine, Daunorubicin, Degarelix, Desferrioxamine Mesilate, Doxorubicin (Adriamycin), Epirubicin, Erythrocin lactobionate, estrogen, Gemcitabine, glucagon, human chorionic gonadotropin, human growth hormone, human menopausal gonadotropin (HMG, menotrpin), human plasma, HcG 5000IU-5 ml, immune globulin (Carimune, Gammagard®), Interferon beta-1a (Avonex), Intron A (interferon alfa-2b), Kogenate FS (recombinant factor VII) Leucovorin calcium, leuproreline, methylprednisolone, Leukine (sargramostim), Menomune® vaccine, MMR and MMRV vaccines, Peginterferon alfa-2b (PegIntron), Remicade® infliximab, Sermorelin/GHRH6-5 ml, somatropin (Genotropin, Saizen®), Sincalide (Kinevac), thiotepa, Vecuronium bromide, Vfend (voriconazole), Vincristine, Varicella vaccines, and Zostavax.

Some excipients are included in powdered or lyophilized products, such as solubilizers or buffers, may be considered functional excipients. Excipients used in various lyophilized formulations include bulking agents, buffering agents, tonicity modifiers, antimicrobial agents, surfactants and co-solvents, and are well-known in the art. See, e.g., Baheti et al., *Excipients Used in Lyophilization of Small Molecules*, 1 J. Excipients & Food Chem. 41 (2010). Similarly, diluents are well-known in the art, such as water for injection, and often include excipients, e.g., saline or Ringer's solution.

In one embodiment, a method of operation of a mixing syringe prefilled with proximal and distal substances includes the steps of: (a) drawing back on the plunger rod, thereby disengaging the distal end of the plunger rod within the distal seal assembly to open a fluid path between the proximal and distal chambers, which allows flow of the proximal substance from the mutable proximal chamber into the mutable distal chamber, thereby mixing the two substances; (b) continuing the drawing of the plunger until the distal seal assembly and proximal seal meet and lock together (the system now has only one chamber; mixing is complete); and (c) pushing the plunger rod to expel the mixed substances.

In another embodiment, a method of operation of a mixing syringe prefilled with proximal and distal substances includes the steps of: (a) drawing back on plunger rod thereby disengaging the plug seal from the distal seal to open a fluid path between the prefilled chambers (b) inverting the syringe to allow flow of the distal substance from the mutable distal chamber into the mutable proximal chamber, thereby mixing the two substances; (c) continuing the drawing until distal seal assembly and proximal seal meet and lock together (the system now has only one chamber; mixing is complete); and (d) pushing the plunger rod to deliver mixed substances.

In another embodiment, a method of operation of a syringe having a prefilled mutable proximal chamber includes the steps of: (a) drawing distal substance (e.g., drug or diluent) by pulling proximally on the plunger rod while the plunger rod is locked in position such that a valve between the distal and proximal chambers remains closed, creating and filling a mutable distal chamber; (b) rotating the plunger rod to an unlocked position and drawing back on plunger rod to open a fluid path between distal and proximal chambers, which allows flow of proximal substance from the prefilled proximal chamber into the distal chamber in which the distal substance was drawn from step (a), thereby mixing the two substances; (c) continuing to draw the plunger rod proximally until the distal seal assembly and the proximal seal meet and lock together (the system now has only one chamber; mixing is complete); and (d) pushing the plunger to deliver mixed drug substances.

In yet another embodiment, a method of operation includes the steps of: (a) drawing a distal substance (e.g., drug or diluent) into distal chamber by pulling on the plunger rod to create mutable distal chamber; (b) disabling the locking feature that locks motion of the plunger with motion of the proximal seal thus disengaging the proximal seal from the plunger rod; (c) drawing back on plunger rod to allow flow of the prefilled proximal substance into the distal chamber thereby mixing the proximal and distal substances; (d) continue drawing the plunger rod proximally until the distal seal assembly and proximal seal meet and lock together (the system now has only one chamber; mixing is complete); and (e) pushing the plunger to deliver mixed substance.

An alternative method of operation of a mixing syringe having a prefilled proximal chamber includes the steps of: (a) drawing a distal substance into the mutable distal chamber by pulling on the plunger rod; (b) pushing on the plunger to expel the distal substance; (c) optionally, repeating steps (a) and (b); (d) drawing a distal substance into the mutable distal chamber; (e) disabling a locking feature to allow fluid communication of the proximal substance from the mutable proximal chamber; (f) pulling proximally on the plunger rod to displace the proximal substance until the distal seal assembly and the proximal seal meet and lock together, resulting in fully mixed substance; and (g) pushing the plunger to deliver the fluid.

Yet another alternative method of operation of a mixing syringe having a prefilled proximal chamber includes the steps of: (a) drawing a distal substance into the mutable distal chamber by pulling on the plunger rod; (b) optionally, pushing on the plunger to expel the distal substance; (c) optionally, repeating steps (a) and (b); (d) drawing a distal substance into the mutable distal chamber; (e) disabling a locking feature to allow fluid communication of the proximal substance from the mutable proximal chamber; (f) repeatedly (e.g., at least once) alternately pulling and pushing the plunger rod to mix and expel successively mixed substances comprising a successively less concentrated distal substance/successively more concentrated proximal substance; (g) pulling proximally on the plunger rod to displace the proximal substance until the distal seal assembly and the proximal seal meet and lock together, resulting in fully mixed substance, in which the substance comprises different concentrations of distal and proximal substances compared to a method in which step (f) was not practiced; and (h) pushing the plunger to deliver remainder of the mixed fluid.

Referring to the figures, FIG. 1A shows an embodiment of a preloaded mixing syringe 10 having a housing comprising housing 20, configured similar to a typical syringe. The housing can be glass or plastic or any substance suitable for use in the storage of pharmaceutical-grade substances as are known in the art. Housing 20 contains a first, distal substance 70 in a mutable distal chamber 75, and a second, proximal substance 72 in a mutable proximal chamber 73, mutable chambers are defined by a position of distal seal assembly 40 and a position of the proximal seal 60 within housing 20. The distal end 22 of housing 20 generally has a reduced diameter opening forming a discharge opening. Distal end 22 of housing 20 typically comprises means to maintain the distal end closed, capped or covered, for example by tip cap 23, such that and the syringe contents are maintained in aseptic condition, and means to attach the mixing syringe to a hypodermic needle, luer lock, or suitable engagement for delivery of contents to the desired target. The distal end of the barrel may have a needle, cannula, or other conduit for fluid transfer to a user, to an intravenous (i.v.) line, fluid tube, or container, or the like. In at least one embodiment, the distal end of the barrel has a luer type connection, such as a luer lock connection, for connection of the barrel to a drug container, needle, or i.v. line. The proximal end of housing 20 is configured to receive and house plunger rod 30, axially displaceable within the barrel of housing 20, distal seal assembly 40 and proximal seal 60. The proximal end of housing 20 of the mixing syringe includes a radial flange 21 that may comprise a continuous circumferential flange or be pair of opposing flanges, projecting outwardly from housing 20, and forming a gripping element. It should be noted, however, that the embodiments herein are not limited to any particular type of syringe housing, as the features of the mutable chambers defined by the valved distal seal assembly or proximal locking mechanism are adaptable to a variety of syringe housings.

Plunger rod 30 can be glass, plastic, plastic coated with silicon oxide or plastic coated with barrier coatings such as parylene and the like, or any suitable material typically known in the art. The distal end of plunger rod 30 comprises plug seal 32 (or similar means) configured to displaceably engage a cavity within ring seal assembly, and which serves to maintain closure of the valve mechanism until displaced by an operator to allow mixing of substances 70 and 72. The proximal end of plunger rod 30 comprises grip 39 that projects outwardly as a circumferential flange from plunger rod 30 and provides a gripping element for the operator to use for manipulating the position of plunger 30. Proximal seal 60 is an elastomeric element displaceably situated proximally within housing 20 and configured to engage with distal seal assembly 40 when distal seal assembly 40 is in the most-proximal position, thereafter pressure on plunger grip 39 in the axial, distal direction moves plunger rod 30 and both proximal 60 and distal 40 seals in the distal direction and expels contents of syringe 10 through opening 22 on distal end of housing 20.

Distal seal assembly 40 comprises ring seal 42, an elastomeric element comprising circumferential ribs 43 that forms a fluid-tight seal with the interior wall of the housing 20, and maintains a first substance 70 in a mutable distal chamber 75 that is defined by the position of distal seal assembly 40 within housing 20. Ring seal 42 and distal ribs 43 are configured to be moved axially within housing 20 when sufficient pull or push is applied to plunger rod 30, typically at grip 39. The grip of the plunger rod can be a flange, a ring, or any structure that allows the end-user to move the position of the plunger within the housing of the syringe.

In an embodiment of the invention, as shown in FIG. 1A, distal seal assembly 40 includes ring seal 42 and insert 50, configured to engage plug seal 32, which plug seal 32 is connected with or mounted to the distal end of plunger rod 30. Insert 50 can be made from polymer (e.g., plastic) or glass that is resilient to deformation. In the embodiment of FIG. 1A, distal seal assembly 40 also contains at least one passage 54 extending longitudinally through the interior of insert 50, configured to allow substance 72 to flow or otherwise move from proximal chamber 73 and mix with substance 70 in distal chamber 75, or vice versa, when passage 44 is opened by displacement of plug seal 32 from a distal position "closed" (FIG. 1A) to a proximal position "open" (FIG. 1B) within the distal seal assembly 40. In other words, passage 44 is closed when plunger rod 30 is in its farthest distal position within distal seal assembly 40 and plug seal 32 is engaged with or tightly abutted to the distal portion of ring seal 42, or most-distally disposed within insert 50, as shown in FIG. 1A. In the configuration shown in FIG. 1A, the first 70 and second 72 substances are unable to contact each other when plug seal 32 is in the distal-most position within distal seal assembly 40 (e.g., the most distal position within ring seal 42 and insert 50). The first 70 and second 72 substances can be mixed to form mixed substance 78, however, by displacement of plunger rod 30 axially in the proximal direction P, as shown by the arrow in FIG. 2B, such that plug seal 32 is displaced within ring seal 42 or insert 50 to open passage 54. In at least one embodiment, the proximal seal is retained in a substantially fixed position within housing 20 until connection with the distal seal for delivery of the mixed substance 78, or when the proximal substance and distal substance are mixed, or the delivery of proximal substance 72.

The force required to displace plug seal 32 from the closed position to the open position is less than or equal to the force required to displace distal seal assembly 40 within housing 20. Thus, the user or operator should not be able to easily displace the distal seal assembly when the valve is closed. Although plunger rod 30 and plug seal 32 are configured to be retracted within the ring seal 42, plunger rod 30 remains engaged with distal seal assembly 40, being restricted within a compartment within insert 50, such that once the passage 54 is opened by displacement of plug seal 32 within ring seal 42, the entire distal seal assembly 40 can be moved axially within housing 20, for example in the proximal direction P by proximal movement of the plunger, as shown in FIG. 1C. Movement of distal seal assembly 40 within housing barrel 20 by axial, proximal movement of plunger rod 30 also forces displacement of substance 72 from the shrinking proximal chamber 73 into growing distal chamber 75 via passage 54, until the mutable chambers have merged into one chamber and substances 70 and 72 have mixed to form mixed substance 78.

When plunger rod 30 is moved fully to the proximal end of housing 20, as shown in FIG. 1D, the mutable distal and proximal chambers have merged within housing 20, which then contains mixed substance 78; and distal seal assembly 40 engages proximal seal 60. The engagement between distal seal assembly 40 and proximal seal 60 is such that when plunger rod 30 is moved from the fully proximal position, axially in the distal direction D, as indicated by the arrow in FIG. 1E, both distal seal assembly 40 and axial seal assembly 50 move in unison and expel mixed substance 78 through the distal end 22 of housing 20.

Figure 2A:
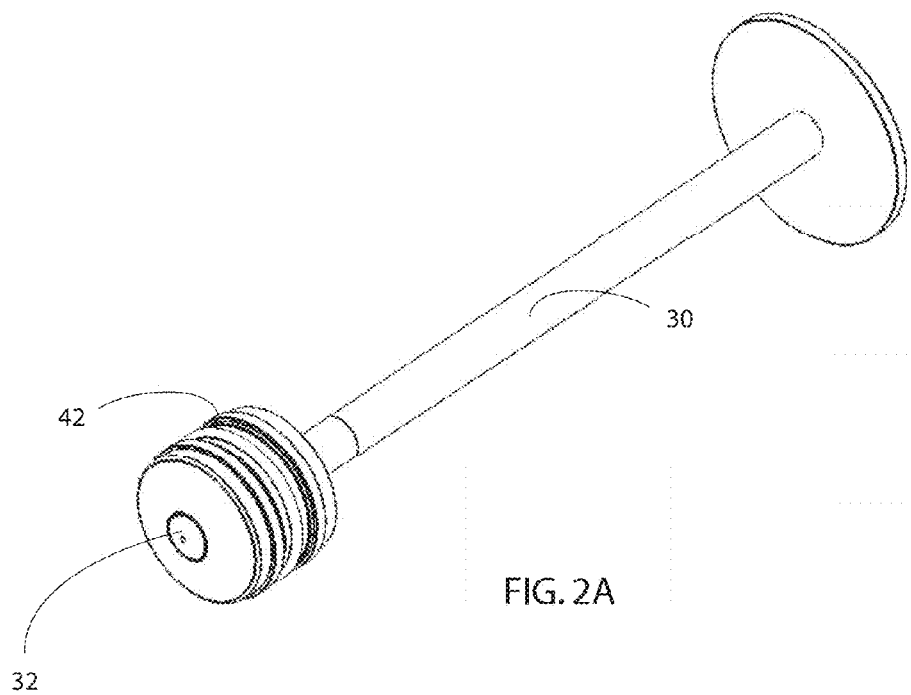
FIG. 2A and FIG. 2B are perspective views showing an embodiment of a plunger rod distal seal assembly, comprising a plug seal in communication with a ring seal, in which the ring seal is in the closed and open positions, such that the passage is closed (FIG. 2A), then opened (FIG. 2B).
Figure 2B:
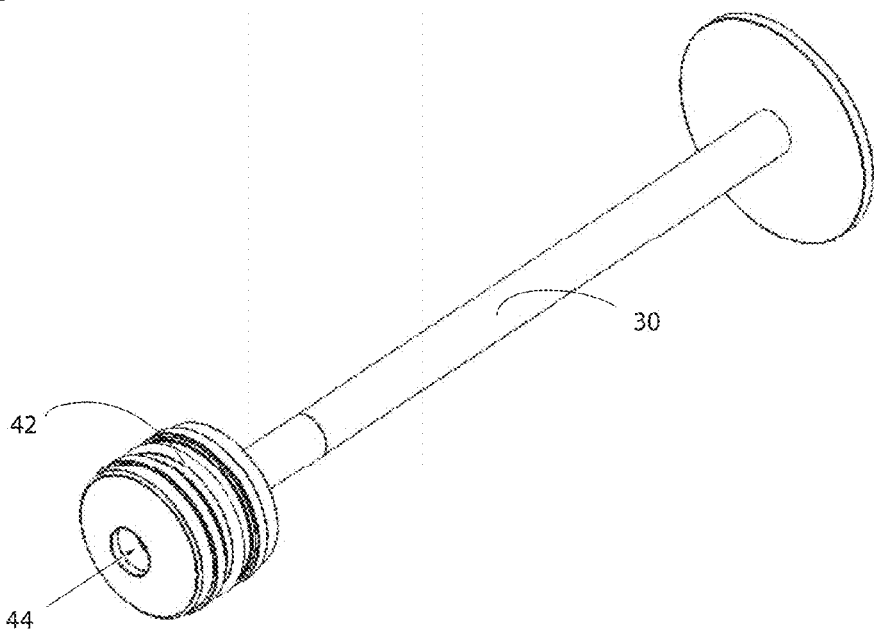

FIG. 2A shows a perspective view of an embodiment of plunger rod 30 and distal seal assembly 40, in which plug seal 32 is positioned at the distal end of ring seal 42 in the closed position. FIG. 2B shows a view of plunger rod 30 and ring seal 42 in which passage 44 is open (the plug seal has been displaced proximally, i.e., retracted, into ring seal 42). Distal seal assembly 40 may comprise a circumferential O-ring or lip in the circumferential ribs 43 that bear against the inner wall of housing 20 (not shown) to create greater resistance to, and regulation of, movement of distal seal assembly 40 compared with retraction of plug seal 32.

Figure 3A:
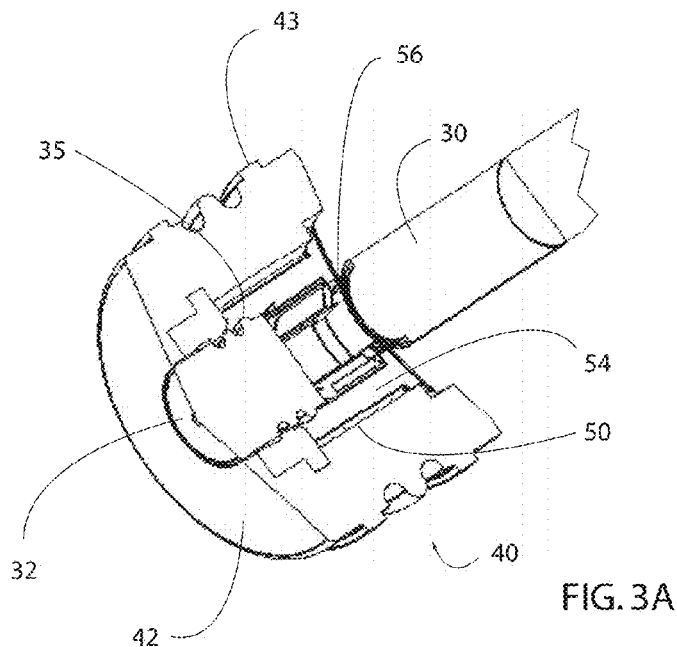
FIG. 3A and FIG. 3B present detailed cross-sectional perspective views of an embodiment of the distal seal in which the plug seal is in the closed position (FIG. 3A) and the open position (FIG. 3B).
Figure 3B:
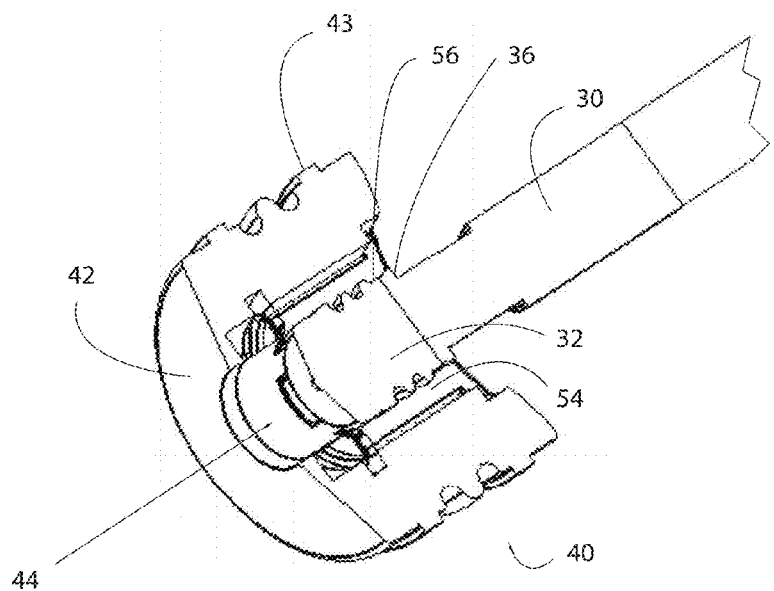

FIG. 3A and FIG. 3B show detailed perspective views of and embodiment of a distal seal assembly 40. Ring seal 42 comprises circumferential ribs 43 configured to bear against the interior of the housing 20 wall (not shown) and provide a fluid-tight seal between distal seal assembly 40 and inside wall of barrel housing 20, and resistance against accidental movement of distal seal within barrel of housing 20. Movement of distal seal 40 within housing 20 can also be impeded by vacuum or pressure in the appropriate distal or proximal chambers. When plug seal 32 is disposed in ring seal 42 in the "closed" position, plunger rod 30 can be displaced proximally relative to ring seal 42, but plunger rod 30 cannot be further displaced distally relative to the distal end of distal seal assembly 40. For example, motion of plug seal 32 can be limited within ring seal 42 by configuration of complementary facing tapered distal ends of the exterior of plug seal 32 and interior of ring seal 42; or by placement of a threaded connection, interior-facing projections, or other structures. For example, ring seal 42 is fitted with insert 50, which is stabilized within ring seal 42 by a protrusion fitting 55 that fits in a complementary recessed step 45 within ring seal 42. Plug seal 32 is connected to plunger rod 30 by conventional means, such as glue or complementary screw threads or snap-lock engaging means. Plug seal 32 comprises exterior annular ribs 35 that releasably engage the interior of insert 50 by means structures such as a protrusion and recess or threaded screw, or plug seal 32 and annular ribs 35 may simply bear against the interior wall of insert 50 such that movement is impeded until the user engages in proximal displacement of plug seal 32. Prior to use (i.e., prior to mixing), annular ribs 35 of plug seal 32 block passage 44 and the first and second substances cannot mix. To prepare the device for use, i.e., initial mixing of proximal substance 72 with distal substance 70, the operator displaces plunger rod 30 proximally relative to distal seal assembly 40, typically by pulling on plunger rod grip 39, thereby displacing plug seal 32 within insert 50 and opening passage 44, as shown in FIG. 3B. In an alternative embodiment, annular ribs 35 and annular steps 45 are configured as complementary male and female threads, such that plug seal 32 is moved from the distal-most position within distal seal assembly 40 by a twisting, limited "unscrewing" motion of plunger rod 30.

Distal seal assembly 40 and plunger rod 30 may also comprise means to impede further proximal motion of plunger rod 30 from distal seal assembly 40 such that plug seal 32 cannot be removed readily from insert 50, and plunger 30 is substantially permanently attached to distal seal assembly 40. For example, as shown in FIG. 4A and FIG. 4B, plunger rod 30 comprises a flanged region or pair of barbs 36, configured to engage a complementary recess 56 in insert 50, such that when plunger rod 30 is moved axially, plug seal 32 is proximally displaced and passage 44 has been opened, barb 36 engages recess 56 which impedes further substantial proximal movement of plug seal 32 within distal seal assembly 40. Alternatively, the device can be configured such that annular rib 35 engages with annular recess 46; via a complementary threaded connection; or via a cross section comprising a series of proximally tapered annular steps that engage complementary annular ribs inside the distal seal assembly 40. Once plug seal 32 has been retracted such that passage 44 is opened, further proximal motion of plunger rod 30 moves entire distal seal 40 in the proximal direction within the barrel of housing 20.

Figure 4:
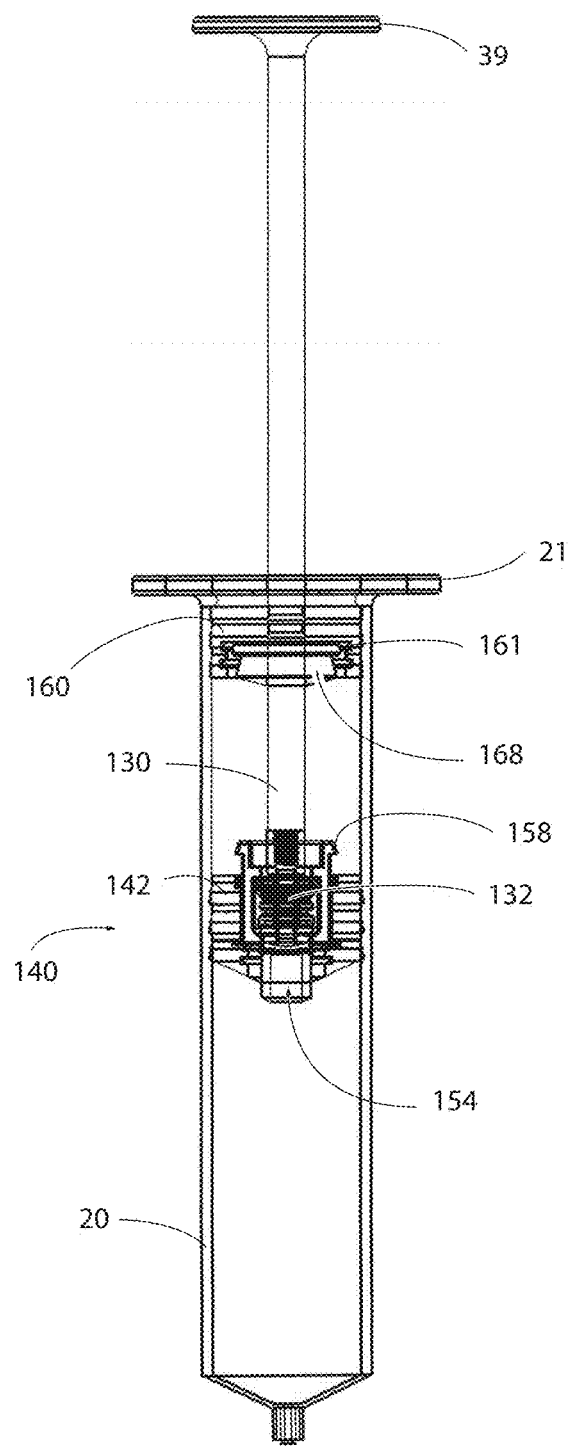
FIG. 4 shows a cross-sectional view showing an embodiment in which the distal seal assembly and proximal seal assembly comprise a locking mechanism.

Referring to FIG. 4, in this embodiment distal seal assembly 140 comprises ring seal 142, which holds an insert having a fluid passage 154 that is opened when plug seal 132 is in the proximal position (as shown), and further comprises projecting connector 158 configured to mate with a complementary recessed connection 168 formed in proximal insert 161 in proximal seal 160. The connector may comprise other proximal seal engaging means, such as complementary screw threads or a snap-lock protrusion and complementary snap-lock recess to form a locking mechanism that facilitates connection of distal seal assembly 140 and proximal seal 160, such that once engaged by motion of plunger rod 130 to the most-proximal position, seals 140 and 160 are irreversibly joined and then respond in tandem to depression of plunger rod 30, similar what is shown in FIG. 1E.

Figure 5A:
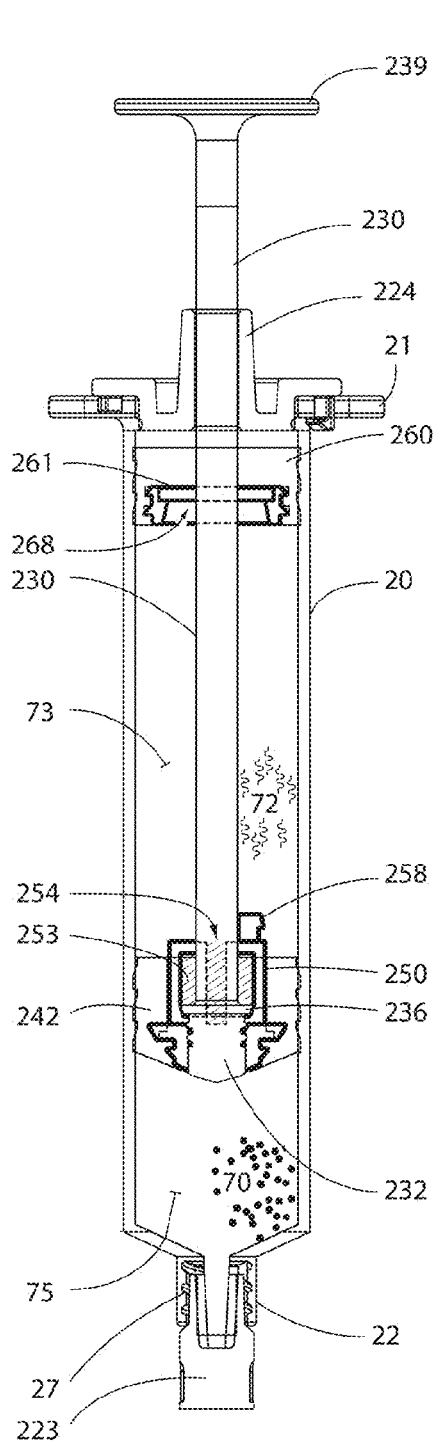
FIG. 5A to FIG. 5F depict cross-sectional views of an embodiment of the mixing syringe of the invention in several stages of use.
Figure 5B:
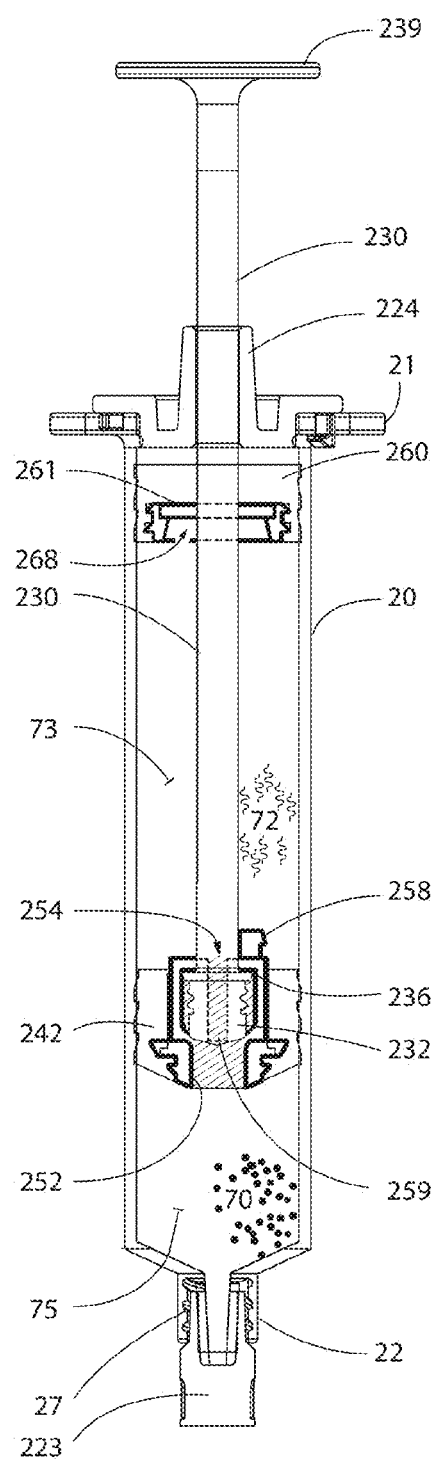

Another embodiment of distal and proximal seal assemblies of the mixing syringe are shown in FIG. 5A to FIG. 5F, with details of the distal ring seal, insert and plug seal illustrated in FIG. 6A and FIG. 6B. In this embodiment of a preloaded syringe, plunger rod 230 includes engaging means 231 in the form of a complementary screw/thread in plug seal 232, which engages plunger rod 230 with plug seal 232, as shown in FIG. 6C. Plunger 230 further comprises a radial collar or flange 236, configured to limit movement of the plug seal within the confines (interior compartment) of insert 250 and maintain the connection between plunger rod 230 and distal seal assembly 240. Note that the mixing syringe of FIG. 5A is depicted with stopper 223 positioned in the distal end 22 of barrel housing 20, which is replaced by needle assembly 28 in FIG. 5F, in which mixed substance 78 is injected, via threads 27. The embodiment shown in FIG. 5 also comprises a syringe cap assembly 224 abutting flanged grip 21 and sealing the prosimal end of the mixing syringe. FIG. 5A and FIG. 6B show the distal seal assembly is in the "closed" position, in which plug seal ribs 235 bear against distal channel 252 formed by the interior wall of insert 250, which channel is visible once the plug seal is moved into the "open" position as shown in FIGS. 5B and 6B. Further distal movement of plug seal 232 is impeded by distal edge 257 formed by the interior walls of insert 250, which stops radial flange 236 from distal movement within insert 250. Insert 250 is stabilized within ring seal 242 by at least one protruding radial flange or shoulder 255 that fits into complementary ring seal step 245.

In the view of FIG. 5B and FIG. 6B, proximal motion of plunger rod 230 has displaced plug seal 232 from channel 252 and into channel 253 (hashed in FIG. 5A) in insert 250. Distal seal assembly 240 maintains position in housing 20 by pressure of radial ribs 243 against the interior wall of housing 20. The position of plug seal 232 away from channel 252 and into channel 253 (i.e., retracted into the distal seal assembly) unblocks opening 259 in passage 254 (hashed), such that the valve function of distal seal assembly 240 is "open," which allows communication between mutable distal chamber 70 and mutable proximal chamber 80. Further proximal motion of plunger rod 230 is impeded by plunger rod flange 236 abutting proximal ledge 256 of the insert compartment formed by the proximal interior wall of insert 250.

Figure 5C:
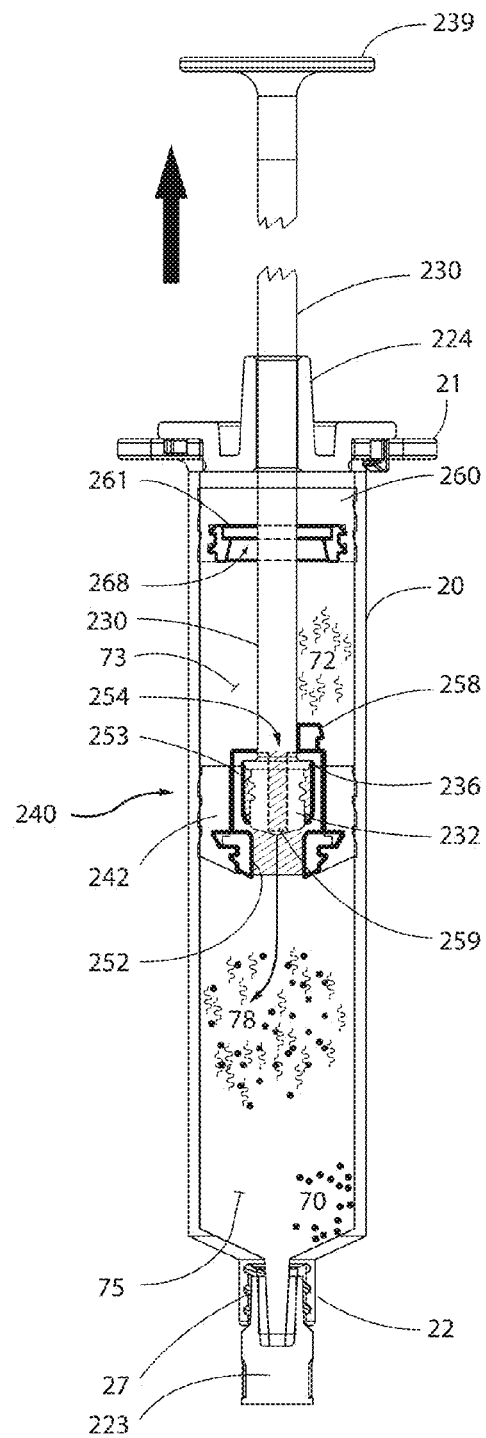
Figure 5D:
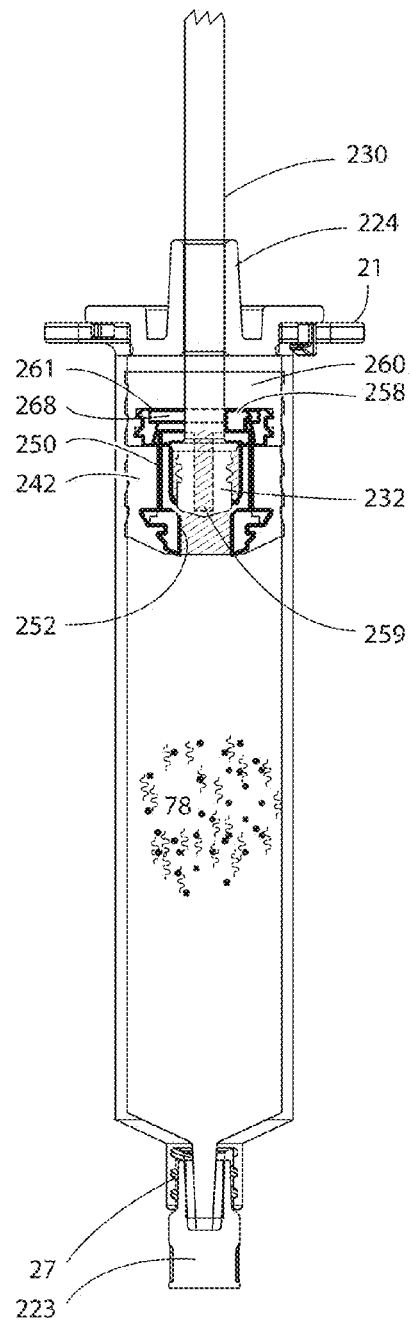

As shown in FIG. 5C, once passage 254 has been opened, the user may continue to displace plunger rod 230 in the proximal direction, which in turn displaces seal assembly 240 in the proximal direction, displacing substance 72 from the shrinking proximal chamber 73 through passage 254 and into growing distal chamber 75, such that substance 72 combines with substance 70 to form mixed substance 78. In this embodiment, the user is not able to pass substance 78 back through passage 254 as a means of mixing, because distal pressure of plunger rod 30 may close the valve before distal assembly 240 moves in the distal direction. In alternative embodiments, however, displacement of a distal plug seal can be achieved using a locking mechanism, e.g., a screw-thread mechanism or snap-lock mechanism, such that the open position remains fixed during subsequent distal pressure on plunger rod 30. In the embodiment of FIG. 5D, if required to ensure adequate mixing, the user can shake, swirl or vortex the syringe to achieve substantial or complete mixing, dissolving, dispersing or suspending of mixed substances 78.

Also shown in the FIG. 5 series is a connecting mechanism, connector 258, configured to connect distal seal assembly 240 with proximal seal 260, further details of which are shown in FIG. 6C. In this embodiment, the connection between distal seal assembly 240 and proximal seal assembly 260 is configured to be permanent or otherwise difficult to dislodge. Proximal seal assembly 260 comprises radial ribs 263, which bear against the inner wall of housing 20 to impede movement of proximal seal 260 until the operator engages it with distal seal assembly 240. Proximal seal 260 comprises rigid insert 261 held in place within proximal seal 260 by protrusions 265 extending outwardly therefrom into complementary annular steps 264 within proximal seal 260. The interior wall of insert 261 comprises recess 268, a connection configured to receive and connect with connector 258 when distal seal assembly 240 reaches the proximal-most position as shown in FIG. 5D.

Figure 5E:
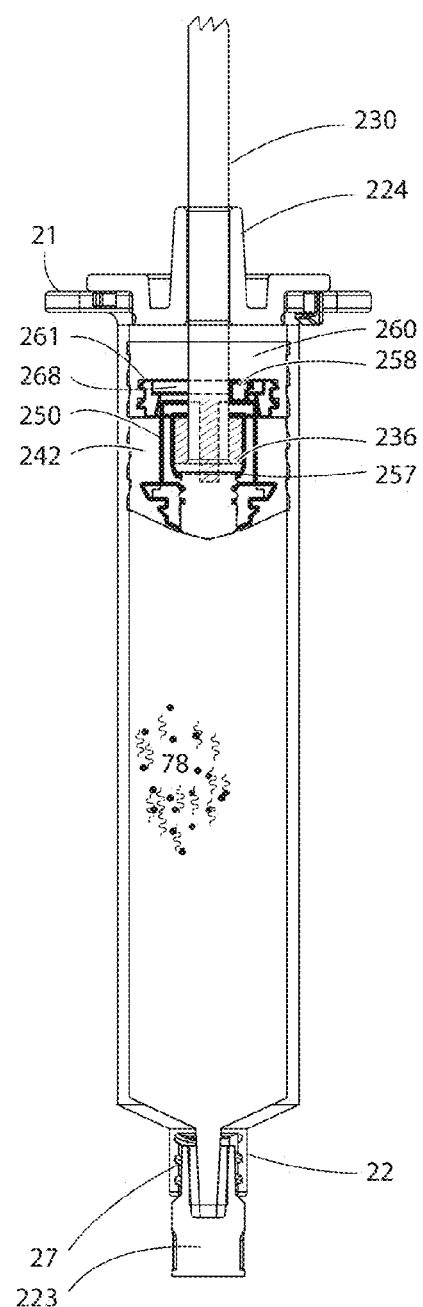
Figure 5F:
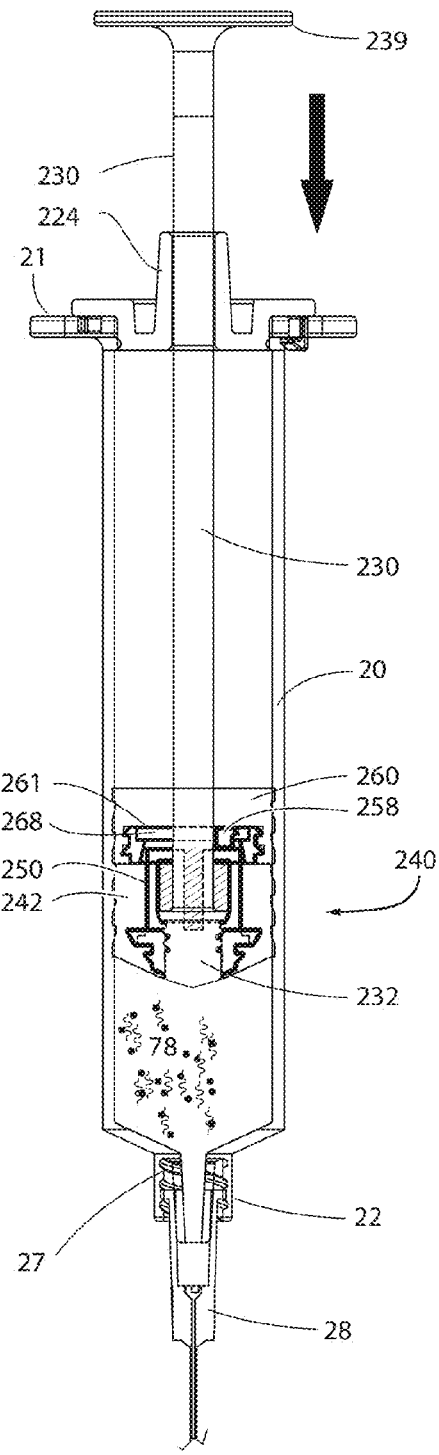

As shown in FIG. 5D, once plunger rod 330 has been maneuvered into the proximal-most position within housing 20, the mutable proximal and distal chambers have merged and housing 20 holds mixed substances 78. In this position, plug seal 232 is still in the proximal open position, although proximal seal 260 is a fluid-tight seal. Proximal displacement has caused connector 258 to mate with connection 268, such that distal seal assembly and proximal seal 260 are connected. Thereafter, to ensure that little or no substance 72 or mixed substances 78 remains in insert 250, and to close the valve, the user exerts distal pressure on plunger rod 230, for example by depressing plunger rod interface 239, thereby displacing seal plug 232 distally into channel 252, closing passage 244 as shown in FIG. 5E and FIG. 6C. In FIG. 5E, distal seal assembly 240 is locked into connection with proximal seal 260 and the valve is closed; in the position where mixed substance 78 can be expelled from mixing syringe. Thus, the user can now remove cap 23 at the distal end 22 of housing 20 and attach a needle 28, or other suitable device, via threaded screw structure 27 (e.g., a luer lock) in distal end 22 of housing 20, as shown in FIG. 5F. FIG. 5F shows a mixing syringe when mixed substances 78 are being been expelled from the device, which can continue until the distal end of plug seal 232 abuts the distal interior end of the housing. Because of the engagement between connector 258 and connection 268, proximal seal 260 and distal seal assembly 240 are connected such that distal pressure against plunger rod 230 by depressing 239 has displaced the two seals as a single seal unit as mixed substances 78 are expelled via needle assembly 28.

FIG. 6A to FIG. 6C show detailed views of the example embodiment of distal seal assembly 240 in the closed (FIG. 6A and FIG. 6C) and open (FIG. 6B) positions. In this embodiment, distal seal assembly 240 comprises seal ring 242, which houses insert 250 which, in turn, houses plunger rod 230 and plug seal 232. Seal ring 242 includes exterior, radial circumferential ribs 243 that bear against the interior wall of housing 20, forming a substance-proof seal. Seal ring 242 further includes internal annular steps 245, into which fit a radial flange 255 extending outwardly from insert 250, such that the position of insert 250 is fixed within seal ring 242 of distal seal assembly 240. Insert 250 also includes connector 258, configured to mate with recess 268 in insert 261 of proximal seal 260. The interior surfaces of insert 250 form internal compartment 253, which allows limited axial movement of plunger rod 230 and plug seal 232; and passage 254, which allows substance to flow when plug seal 232 is moved in the proximal position within insert 250 (FIG. 6B). Regarding the movement of plunger 230, the interior surfaces (i.e., the internal compartment) of insert 250 form distal ledge 257 and proximal ledge 256, which stop movement of plunger rod 330 within insert 250 by abutting plunger rod flange 236, which extends outwardly from plunger rod 230 at its junction with plug seal 232. Between proximal ledge 256 and distal ledge 257, the interior surface of insert 250 forms channel 253 in which flange 236 can move axially. The interior surface of insert 250 also forms an inner wall 252, which holds plug seal 232 in the closed position (FIG. 6A and FIG. 6C) in which exterior annular ribs 235 of plug seal 232 bear against inner wall 252 to form a substance-tight seal; and inner wall 252 thus defines the distal opening 259 for fluid passage 244 (FIG. 6B) when plug seal 232 is proximally displaced within insert 250. Insert 250 comprises passage 254, through which a substance cannot pass when opening 259 is blocked by plug seal 232 (FIG. 6A and FIG. 6C), but through which a substance can pass when plug seal 232 is moved proximally and thus away from opening 259 (FIG. 6B). In this particular embodiment, plunger rod 230 connects to plug seal 232 via complementary threaded screw 231 (FIG. 6C).

The embodiments described in FIG. 1 to FIG. 6 can further comprise a connection aspect for connection to a needleless access device, such as an i.v. line or to a needle assembly. The connection aspect may be pre-formed as a distal portion of the syringe barrel housing. Alternatively, the syringe barrel may be a substantially straight barrel to which a connection adapter is mounted. An adapter mountable to a syringe barrel may have a luer connection portion and a barrel-engaging portion and a fluid aperture therethrough. The adapter facilitates mounting a luer assembly to the barrel. The luer assembly may be a tip cap having a corresponding female luer fitment for connection to the male luer fitment of the luer connection portion of the adapter. The luer assembly may alternatively be a luer needle assembly having a needle body, cannula, and a needle tip having a corresponding female luer fitment for connection to the male luer fitment of the luer connection portion of the adapter. The term male and female may be used interchangeably to describe corresponding components or aspects thereof. The adapter and syringe further comprise an immobile, compressible needle seal. The needle seal is adjacent to or engageable with the barrel-engaging portion of the adapter. The needle seal sits within the interior of the barrel or adapter, and has a fluid pass-through axially located for the passage of fluid.

Figure 7A:
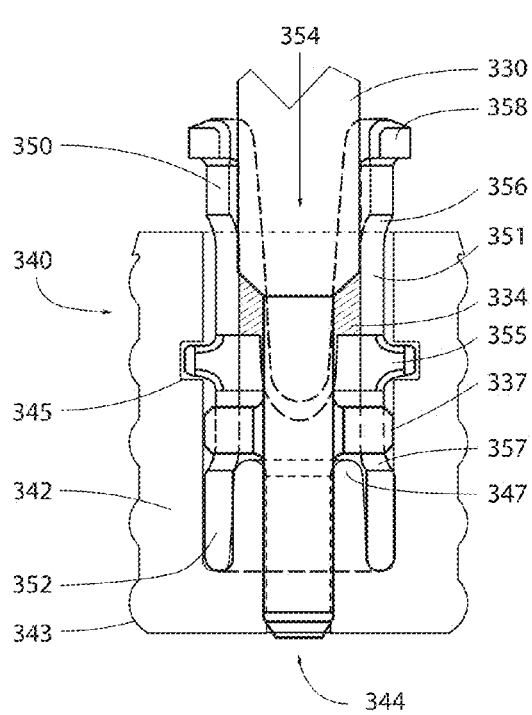
FIG. 7A to FIG. 7E illustrate detailed cross-sectional and isometric views of an embodiment of distal seal assembly and its components.
Figure 7B:
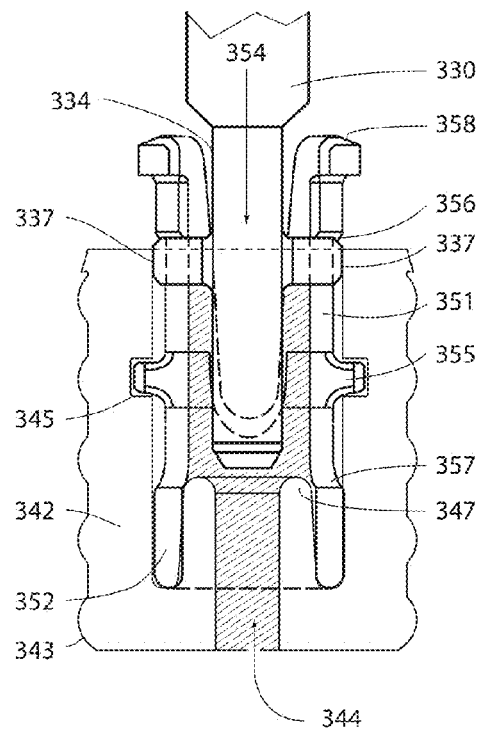
Figure 7C:
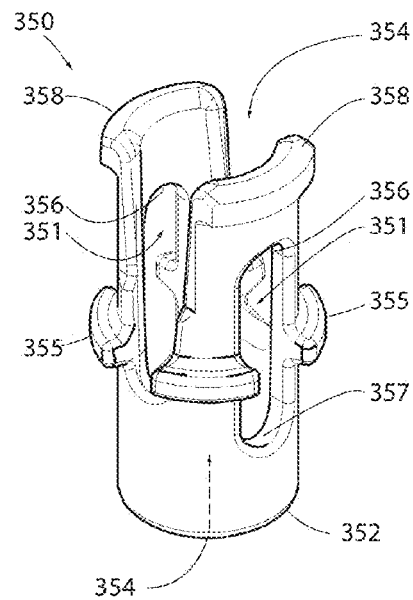
Figure 7D:
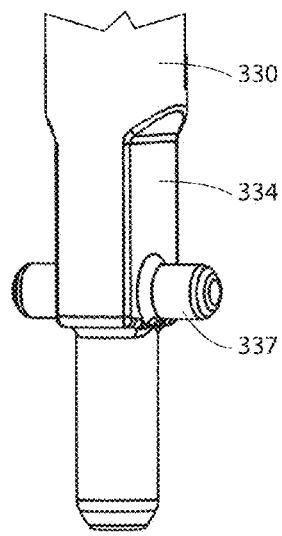
Figure 7E:
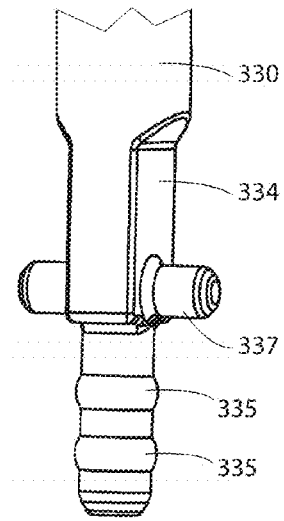

FIG. 7A to FIG. 7E are detailed views of another embodiment of a distal seal assembly and its components. In the embodiment shown in FIG. 7A, distal ring seal 342 comprises exterior rings 343 configured to bear against the inner wall of housing 20, and internal step 345 for receiving exterior protrusions 355 that extend radially from insert 350 (FIG. 7C). Plunger rod 330 extends axially in direction (D) through insert 350 and into inner lip formation 347 of elastomeric distal ring seal 342, forming a substance-proof, (e.g., fluid-tight) barrier. Plunger rod 330 may be smooth (FIG. 7D) or comprise circumferential ribs 335 (FIG. 7E). Lip formation 347 is held on the side opposite of plunger rod 330 by inner wall 352 of insert 350. Plunger rod 330 is configured with at least a pair of distal indentations 334 positioned axially along a distal portion of plunger rod 330 (FIG. 7D, 7E), which channels 334 are inaccessible to substances when plunger rod 330 is positioned fully distally within distal assembly 340 (FIG. 7A); but channels 334 are accessible to substances when plunger rod 330 is positioned fully proximally within distal seal assembly 340 (FIG. 7B, FIG. 8B).

Figures 8C, 8D:
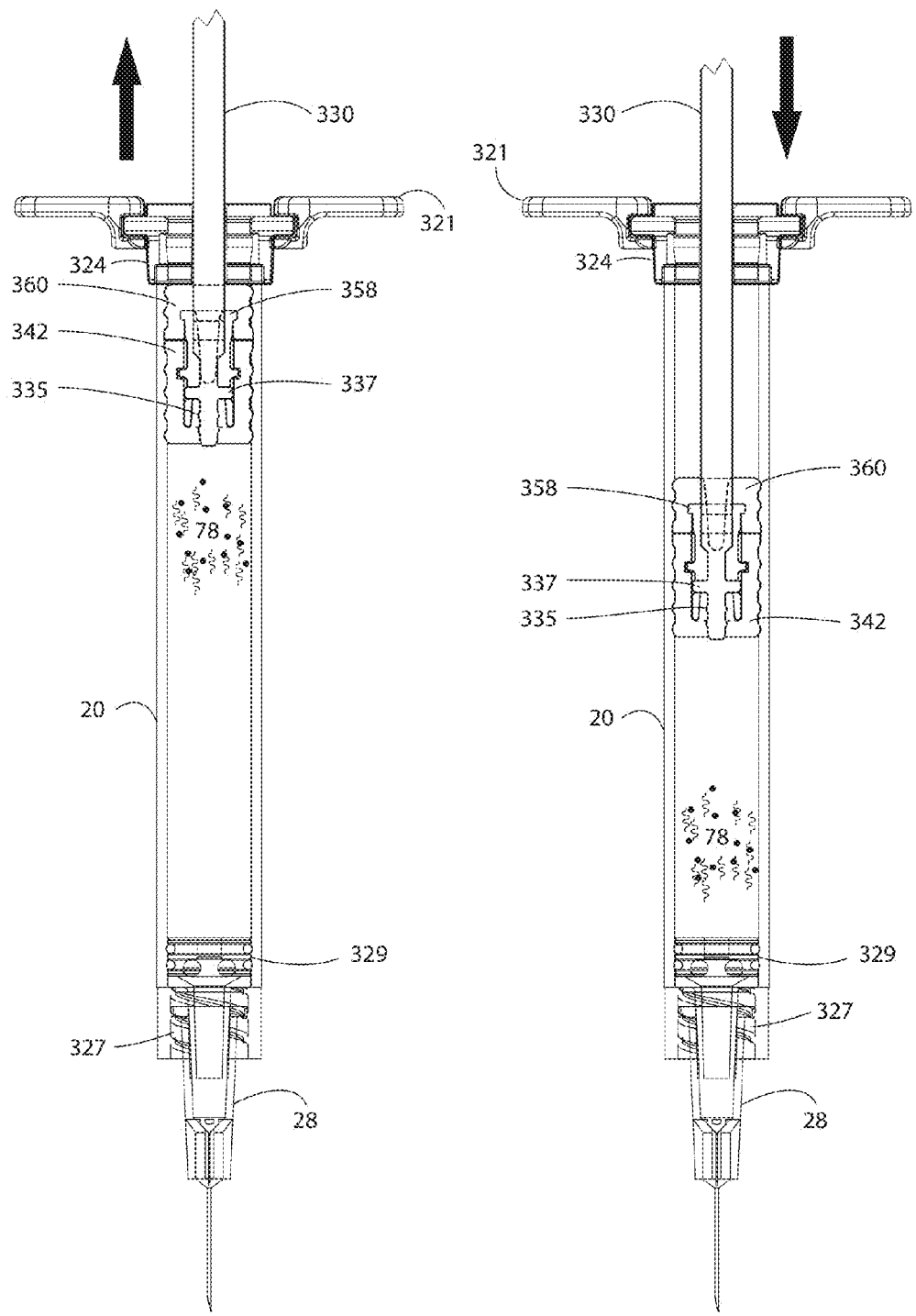

As shown in FIG. 8A, plunger rod 330 may be configured with complementing screw/threads 338 or similar structures for securing plunger rod to a grip, such as pull 339 or a flanged button grip (see FIG. 11, button 439). In this embodiment, plunger rod 330 further comprises a pair of radially extending protrusions 337 (see details in FIG. 7D and FIG. 7E), positioned within a groove or channel 351 positioned longitudinally within insert 350 (FIG. 7C), which allow protrusions 337 limited axial displacement of plunger rod 330 between the distal stop 357 (valve in closed position, FIG. 7A, FIG. 8A) and proximal stop 356 (valve in open position, FIG. 7B, FIG. 8B) in channel 351. Plunger rod 330 may also comprise annular rings 335 (FIG. 7E), configured to bear against the interior lip 347 of distal seal 342 to enhance the substance-proof seal. Insert 350 further comprises substance passage 354, through which substances cannot flow when plunger rod 330 is in the fully distal position within distal seal assembly 350 (FIG. 7A), but which passages 354 allow fluid passage via the indentation 334 in plunger 330 and the narrower distal end of plunger rod 330 when plunger rod 330 has been moved proximally within insert 350 as defined by channel 351 (FIG. 7B). As further shown in FIG. 7B, when plunger rod 330 has been moved axially until abutting proximal stop 356, insert substance passage 354 and an indentation in plunger rod 330 that forms passage 334 allow passage of substances through passage 344 in the distal end of distal ring seal of distal assembly 340. Insert 350 further comprises connector 358 for connecting with a complementary recess in the proximal seal (FIG. 8C and FIG. 8D).

It should be noted that the particular embodiment of the mixing syringe depicted in FIG. 8A to FIG. 8D relates to a prefilled mixing syringe. In these figures, proximal substance appears to be fluid and substance 70 appears as solid particles. This is not a limitation or representation of particular substances, however, but merely a depiction of different substances mixing. Indeed, either mutable chamber can hold solids or fluids as defined herein, and solids could dissolve completely and become liquids, so the intent of these figures is not to limit the substances that can be used in the mixing syringes. As shown in FIG. 8A, the mixing syringe includes a cap 23 in which internal barbs 23(a) help secure its position protecting the distal end of syringe housing 20. Housing 20 further include luer adapter 327, needle seal 329, grip 321, and cap 324 is inserted post-fill on the proximal end of the device. Housing 20 holds plunger rod 330, positioned axially therein and including screw/thread adaptation for connecting with pull 339. Mutable proximal chamber 73, holding substance 72, is defined by the positions of proximal seal 360 and distal seal assembly 340. Mutable distal chamber 75, holding substance 70, is defined by the position of distal seal 342 and needle seal 329. Distal seal assembly 340 includes distal ring seal 342, which holds insert 350 by the insert's radial shoulders 355, and also engages with plunger rod 330. In this embodiment, plunger rod 330 includes a pair of radial protrusions 337 which are maintained within insert 355 as shown in FIG. 7A and FIG. 7B. In FIG. 8A, as in FIG. 7A, the valve mechanism (the engagement of rod 330, insert 350 and distal ring 342) is shown in the closed position. As shown in FIG. 8B, when the operator is ready to mix the contents of the prefilled syringe, proximal translation (pulling) of plunger rod 330 displaces plunger rod 330 within insert 350 until protrusions 337 abut proximal edges of channels 351 (see FIG. 7B), opening fluid channels 354 and 344, and allowing proximal substance 72 to pass from shrinking mutable chamber 73 and mix with distal substance 70 and form mixed substance 78 in growing mutable distal chamber 75.

As shown in FIG. 8C, maximal proximal translation of plunger rod 330 brings distal ring seal 342 to meet with proximal seal 360, whereby connector 358 of insert 350 connects with connection 368 formed in insert 361 held in proximal seal 360. Once proximal seal 360 and distal seal 342 are connected, distal pressure against plunger rod 330 pushes protrusions 337 into the distal-most position within insert 350, which closes the valve mechanism. Mutable proximal and distal chambers are now merged and mixing is complete. The operator can attach needle assembly 28 at this or a previous step. As shown in FIG. 8D, because distal and proximal seals are connected, distal pressure on rod 330 expels mixed substance 78 through needle assembly 28.

The embodiments described in FIG. 7 and FIG. 8 can further comprise a connection aspect for connection to a needleless access device, such as an i.v. line or to a needle assembly, as described elsewhere herein.

In at least one embodiment, the mixing syringe includes accurate dose control mechanisms, such as those described in WO 2013086167, although the embodiment is not limited to any particular dose control device. A dose control mechanism allows for the accurate dosing and delivery of mixed substances from a mixing syringe, in particular permitting the identification and control of the dosage amount, the "priming" of the syringe (i.e., evacuated of air bubbles) prior to administration or delivery, and ensures the accurate delivery of microliter volume dosages, all within a device size that is similar to commonly used conventional syringes available in the marketplace. The design the dose control mechanism provides for mixing syringes that are safe and easy to use, and are aesthetically and economically appealing for users, without significantly altering technique currently employed by users to deliver injectables. When utilized within a mixing syringe, the control mechanism can be attached to the housing 20 after the mutable chambers 75 and 85 have been filled with substances. This is often desired so that the mixing syringe may be filled and assembled in standard pharmaceutical fill-finish process lines.

FIG. 9A to FIG. 9D presents an exemplary mixing syringe comprising a dose control mechanism. The control mechanism includes control plunger 614, a control housing 620, an adapter 618, and a screw 600. The control plunger 614 includes a button 612 or similar structure as a unified or separate component, but in any case the surface 612 provides a user interface 612A with the device. In at least one embodiment, the control housing has a housing cover at its proximal end and a window to permit the user to view the location of the control plunger within the housing. The control plunger may have one or more dose markings on the external surface of the plunger and the housing may have one or more guide markings with which to align plunger dose markings. Control housing 620 may optionally include housing cover at its proximal end, for example, to close the interior of the housing 620 off from the environment or to axially align plunger 614 within control housing 620. Control housing 620 may further include a window 620A, which may be an opening (e.g., an aperture) in the housing or a transmissive, translucent or optically magnifying component. Control plunger 614 may include one or more dose markings on the external surface of the control plunger. Housing 620 may have one or more reference or guide markings, such as at the window 620A, with which to align plunger dose markings.

The control mechanism includes control plunger 614 having coarse pitch screw 614B on its exterior surface, with control housing 620 having a corresponding coarse pitch guide 620C along the interior surface of the housing 620. Screw 600 has fine pitch screw 600B, which interfaces with fine pitch nut 618B of adapter 618, wherein the control plunger 614 has an internal annular space 614C within which screw 600 at least partially resides. The control plunger 614, having the coarse pitch 614B (visible in FIGS. 9A and 9C) is rotatable upon the corresponding coarse pitch guide 620C, and wherein at least a portion of the control plunger 614 is rotationally keyed to interface with a corresponding rotationally keyed portion of screw 600. The pitch on guide 620C is the same as pitch on plunger thread 614B. Similarly, screw 600 has a fine pitch thread 600B which interfaces with a fine pitch nut 618B of adapter 618. The control plunger 614 having the coarse pitch 614B is rotatable upon the corresponding (e.g., "female") coarse pitch guide 620C, which is rotationally keyed to the screw 600 having the fine pitch thread 600B. The terms "male" and "female" are intended to describe corresponding or complementary and interfacing threads or surfaces, and can be used interchangeably to describe corresponding aspects as would be readily appreciated in the art. Screw 600 having fine pitch screw 600B engages female fine pitch nut 618B of adapter 618. Upon use by the user, plunger axially translates a first distance D1 causing screw to axially translate a second distance D2, wherein D1 is always greater than D2 by a factor determined by the pitch ratio. Hence, rotation of control plunger 614 results in axial translation of screw 600 and the resolution of axial travel is dictated by pitch 600B.

Because the plunger 614 and screw 600 are rotationally keyed, each having a respective screw pitch, rotational translation of the plunger 614 rotates and axially translates the screw 600. The term "keyed" is used herein to mean any number of internal aspects which removably or slidably (in the axial sense) connect two or more components. For example, the control plunger 614 may be a hollow cylinder having a coarse pitch screw on at least some portion of the outer surface and a spline design along at least a portion of the inner surface. The spline design is configured to mate with, and transform or relay rotation to, a complementary spline contained at a proximal end of the screw. This spline design element ensures that the plunger and screw are rotationally keyed. In the embodiment of FIG. 9, the spline or rotationally keyed aspect is at the proximal end 600C of screw 600, and with its corresponding spline or rotationally keyed aspect in the annular space 614C of plunger 614. Many other shapes and configurations may be utilized to impart a rotationally "keyed" relationship between these components, such that the first component may removably or slidably engage the second component in a manner that enables the rotational keyed relationship and permits axial slip. Such components may alternatively be keyed to have the shape of, for example, a cross or plus, a horizontal line or minus, a star, or a semi-circle shape, with the corresponding component having the inverse of the shape on an interior annular space. This arrangement or configuration allows the two components, screw 600 and control plunger 614, to be rotationally keyed while allowing them to axially slip past each other. Both screw 600 and control plunger 614 reside, at least partially or at some point of operation, within control housing 620.

Figure 9A:
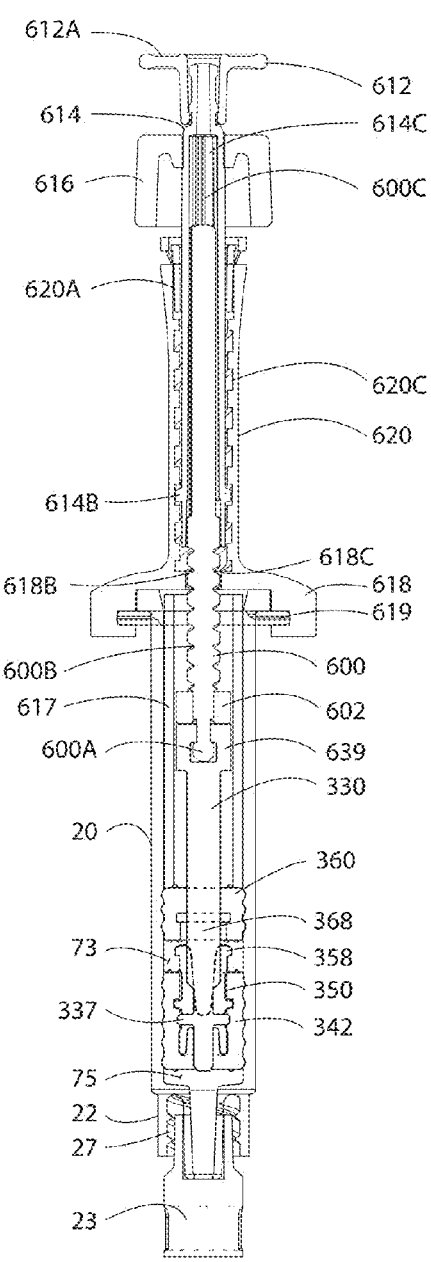
FIG. 9A to FIG. 9D present cross-sectional views of an embodiment of the mixing syringe, comprising a dose control mechanism, in several stages of use.
Figure 9B:
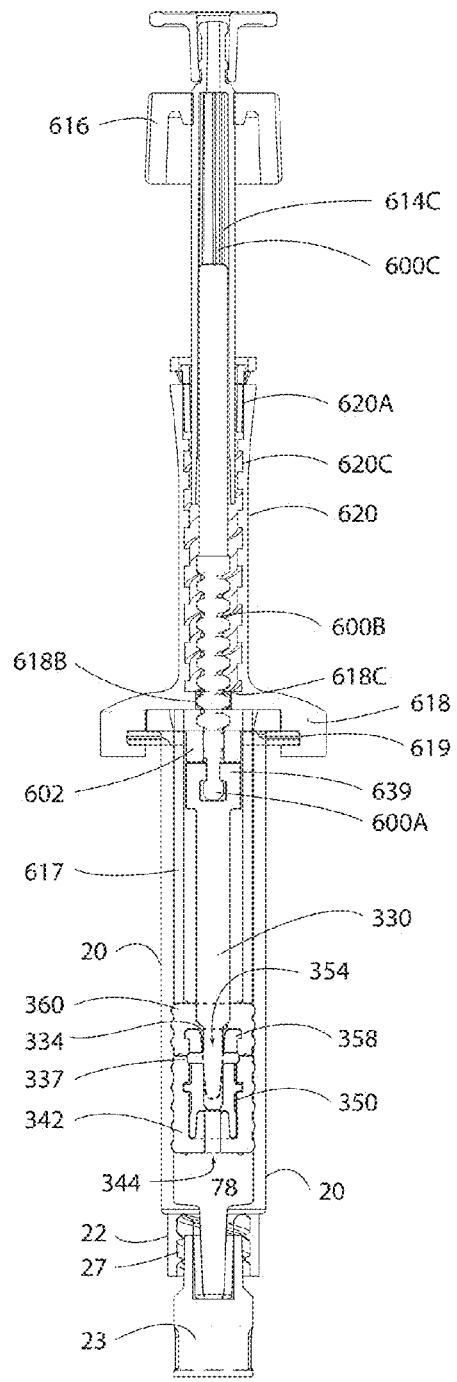

Also visible in FIG. 9A is ledge 618C of adapter 618. Fine pitch nut 618B (or simply "nut"), having the same fine pitch 600B of the screw 600, may be used to brace the screw 600 and facilitate the transfer of the rotational movement of the plunger 614 into axial translation of the screw 600. The pitch ratio of the coarse pitch to the fine pitch dictates the degree or resolution of axial travel of the screw 600, i.e., the distance that the screw 600 axially translates for each rotation of control plunger 614. As a result, the user is provided with an ease of operation that enables them to accurately read and set the dosage amount. The pitch ratio can be set to enable "fine tuning" of the dosage amount, which is of particular importance for low-volume dosage quantities where variance may be significantly affected by plunger travel. A pitch ratio between coarse pitch screw 614B and fine pitch screw 600B is from about 1:1 to about 20:1, for example from approximately 2:1 to approximately 10:1, or from about 4:1 to about 8:1. In a particular embodiment, the pitch ratio of coarse pitch screw 614B and fine pitch screw 600B is approximately 4:1.

The control mechanism may be attached, mounted, affixed, or otherwise connected at the proximal end of the barrel of housing 20, for example via adapter 618 and clip 619, such that at least a portion of the screw 600 resides inside barrel 20. The portion of the control mechanism housed within the standard barrel 20 may be contained in internal spacer 617, which sits between and abuts the proximal side of proximal seal 360 and the distal interior side of adapter 618. Screw 600 may be connected to the proximal end of plunger rod 330, either directly or indirectly, to drive the axial translation of plunger rod 330 by a connection aspect. Thus, for example, screw 600 may further include a screw connection aspect which functions to connect the screw to the plunger rod. For example, distal end of screw 600 may be configured as ball 600A which fits in a socket 639 at the proximal end of plunger rod 330. A further component to a connection aspect, such as a plunger ring 602, may be utilized along screw 600, and proximal to socket 639, as part of the screw connection aspect to align or connect the components. For example, plunger ring 602 may be connected to screw 600. Additionally or alternatively, the connection between screw 600 and plunger rod 330 may be a snap-fit connection, an interference-fit connection, or a number of other connection methods known in the industry.

The connection between the screw 600 and plunger rod 330, when the syringe is employed, is such that screw 600 is permitted to rotate axially while plunger rod 330 and seal assemblies 360/340 remain rotationally fixed. Accordingly, as the control plunger 614 and screw 600 of the control mechanism are axially rotated (e.g., by rotating dial 616) and translated distally (e.g., to prime the needle or discharge the mixed substance), the motion is relayed to the seal assemblies 360/340 which are axially translated in tandem but not rotated.

For use, control plunger 614, screw 600 and plunger rod 330 are translated axially in the proximal direction to open the valve of distal seal assembly, and proximal axial translation continues until connector 358 is engaged with proximal seal 360 such that mutable chambers 675 and 685 have merged and substances are mixed 78, as shown in FIG. 7B. The control mechanism may then be utilized by the user to identify and select drug dose for delivery. For example, in one embodiment a pitch ratio between the coarse pitch and a fine pitch may be 4:1, such that rotationally "screwing" or turning control plunger 614, via dial 616, axially translates the plunger component 614 four times as far as the axial translation of the screw component 600. Accordingly, the user is provided with a significant ease of operation because they may more accurately set the required dosage amount. Such a pitch ratio may be, for example, anywhere from the range of 1:1 to 20:1, as may be necessary to obtain the required accuracy of the low-volume dosage amount. The "dialing-in" or "setting" may be facilitated by the dose markings on the plunger and guide markings on the housing.

Figure 9C:
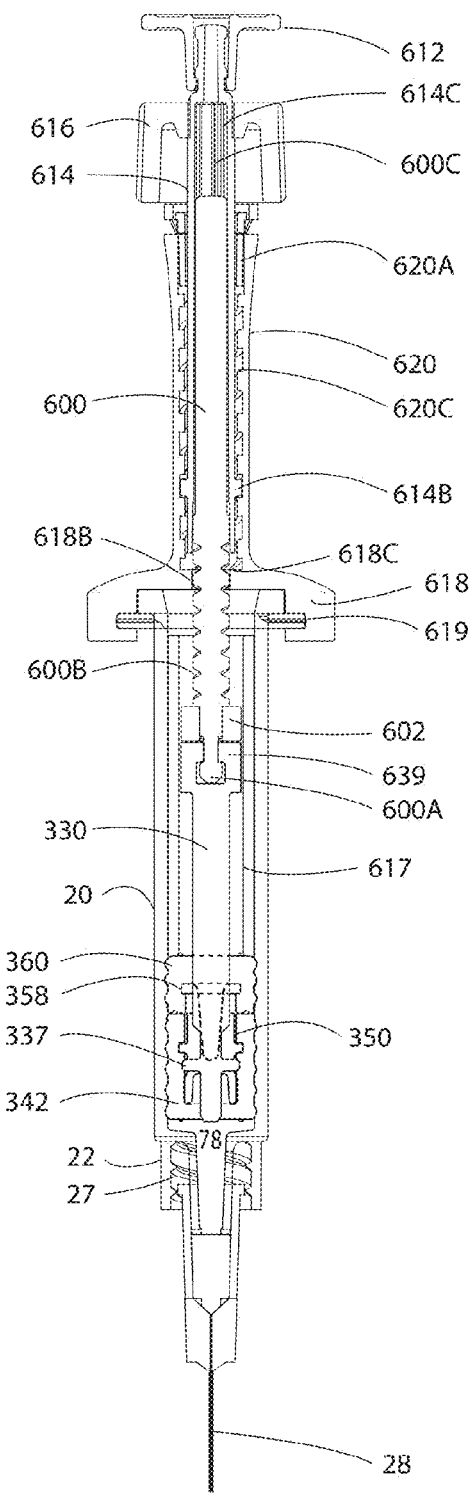
Figure 9D:
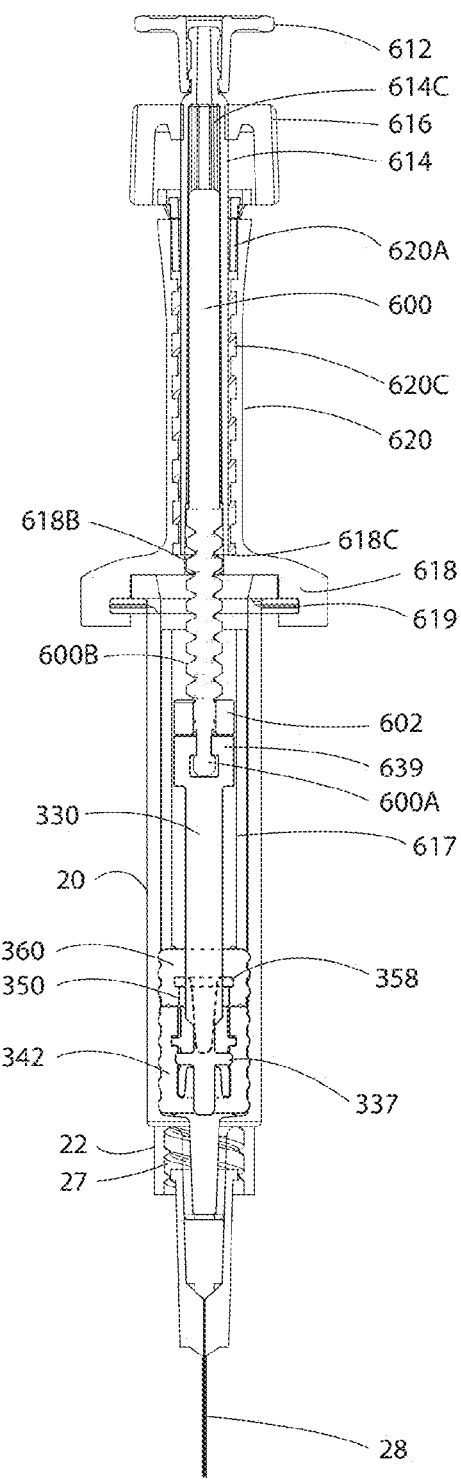

The user may attach needle assembly 28, then axially rotate plunger 614 via dial 616 or depress the button 612 to control the desired dosage volume for delivery as shown in FIG. 9C. Axial rotation of the plunger 614 causes coarse pitch screw 614B to travel within the corresponding coarse pitch guide 620C of housing 620, which causes plunger 614 to axially translate in the distal direction thereby reducing the dosage volume within the drug chamber (i.e., by expelling excess volume). Because of the rotationally keyed interaction between plunger 614 and screw 600 within the annular space 614C, rotation of the plunger 614 causes screw 600 to axially rotate and translate. Because of the pitch ratio between the plunger 614 and screw 600, each unit measure of translation in the distal direction of the plunger 614 results in fractional (e.g., smaller, more resolved) translation of the screw 600 in the distal direction. This has a number of benefits for accurate control during delivery of low-volume doses. Primarily, the pitch ratio relationship permits the user to accurately control the desired dose and delivery of a drug treatment. Additionally, this pitch ratio relationship allows the user to operate a syringe in a conventional manner, such as by depressing the plunger 614 a noticeable distance, while only resulting in fractional or small translation of screw 600 and plunger rod 330. Because of the function of the control mechanism and the pitch ratio, any measure of distal translation of the plunger 614 causes only an incremental measure of distal translation of the screw 600 and plunger rod 330, permitting accurate dose delivery control by the user. Axial translation of the screw 600 causes axial translation of plunger rod 330 and seal assemblies 340/360. This axial motion in the distal direction of the seal assemblies 340/360 force mixed substances 78 out of barrel housing 20 through the needle assembly 28, as shown in FIG. 9D.

The embodiment described in FIG. 9 can further comprise a connection aspect for connection to a needleless access device, such as an i.v. line or to a needle assembly. In this particular embodiment, the ability to provide a universal adapter for connection to a narrow-gauge cannula is advantageous for the delivery of small dose volumes.

As noted, at least one embodiment provides for a mixing syringe in which at least one of the chambers of mixing syringe may be filled just prior to use or at time of use, such as by the physician, pharmacist, nurse, caregiver, patient, end-user, or the like. The fill contents may include materials having viscosity between about 0.25 cP and 2500 cP. Similarly, at least one of the chambers may be pre-filled, while one or more other chambers are filled just prior to use or at time of use. Such an arrangement may be facilitated by the use of one or more locking mechanisms, which enable the valve-type seal in the distal seal assembly to remain closed during some stages of operation, but permit the valve-type seal to open a fluid channel therethrough during other stages of operation. This aspect allows for sequential injection from the distal chamber of a distal substance (optionally more than once), then from the proximal chamber of a proximal substance; or from the distal chamber of a distal substance (optionally more than once), then from the merged distal and proximal chambers of mixed substances.

FIG. 10A to FIG. 10C show an embodiment of a mixing syringe having a locking mechanism incorporated within the distal seal assembly as a configuration of insert 450. In this embodiment, plunger rod 430 comprises a pair of protrusions 437 that extend radially from opposite sides of rod 430 and serve as locking pins that interface with locking groove 451(*a*) of insert 450 (integrated within the distal ring seal). In the locked configuration, shown in FIG. 10A, in which distal end 433 of plunger rod 430 sits in the most-distal position (see also FIG. 11C), distal to insert hub 452, and blocks fluid passage, the distal chamber of the device can be emptied, or filled, or filled and emptied, then refilled, etc., independent of the contents of the proximal chamber. Once locking pins 437 are moved radially (in direction R), such as by rotation of plunger rod 430 out of locking groove 451(*a*) and into channel 451 (as shown in FIG. 10B), the plunger rod can be moved axially (as shown by the arrow in FIG. 10C) from distal end 457 to proximal end 456 of channel 451 (as shown in FIG. 10C); which exposes plunger rod indentation 434 and opens fluid passage 454 within the distal seal assembly, for fluid transfer of the proximal substance from the syringe, or for the mixing of distal and proximal substances. The axis and rotation of the plunger rod in the unlocking motion are shown in the transition from FIG. 10A to FIG. 10B.

Accordingly, in the first locked position, upon proximal translation of the plunger rod, the entire distal seal assembly moves proximally within the syringe barrel in a connected closed arrangement, such as for aspiration or filling of the distal chamber through the distal end of the syringe barrel (for example, for fill-at-time-of-use). In this position, the distal chamber can be filled and emptied (e.g., a dose can be loaded and delivered) sequentially or repeatedly without mixing the distal substance with the proximal substance. Once moved into the second unlocked position the plunger rod may initially translate or move, such as axially translate, thereby opening a fluid passage within the distal seal assembly. As the fluid channel is opened, fluid may pass through the fluid passage for mixing between the first chamber and the second chamber and the plunger rod and distal seal assembly may be moved axially in the proximal direction to enable complete mixing. At the end of the mixing stage, insert connector 458 enables connection of the distal seal assembly to the proximal seal or a proximal seal insert, whereby both the proximal seal and distal seal assembly may be translated axially as a connected, unitary component. Axial translation of plunger rod in the distal direction enables the mixed substance to be pushed out of the syringe, e.g., for delivery to the patient. The locking mechanism also provides a configuration for sequential injection in which the distal substance is expelled, then the valve is opened and translated proximally to mate the distal seal assembly with the proximal seal, which moves the proximal substance into position to be expelled. In other words, sequential delivery of a distal substance followed by a preloaded proximal substance can be achieved without requiring the mixing of substances.

Figure 11A:
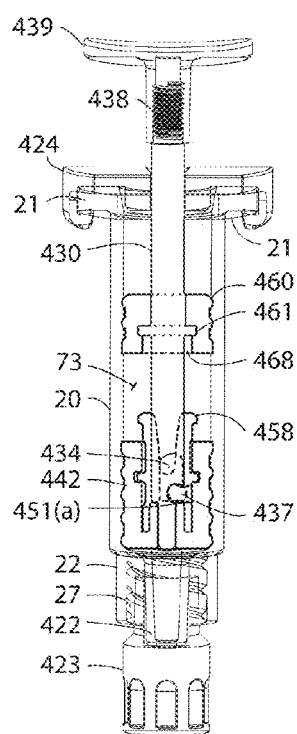
FIG. 11A to FIG. 11G show several views of an embodiment of a syringe in which a locking aspect of the distal valve assembly allows the mutable distal chamber to be filled and emptied independent of the prefilled mutable proximal chamber, providing for sequential delivery of substances from the syringe.
Figure 11B:
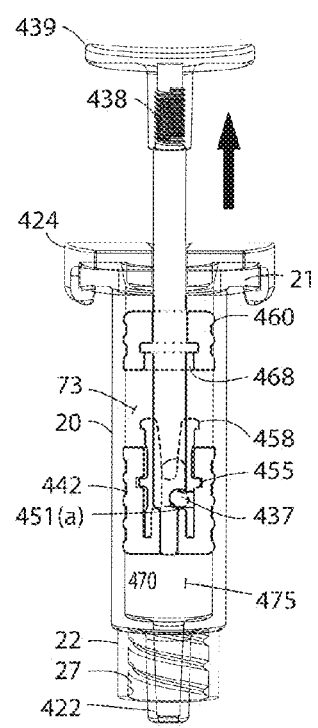

According to the embodiment shown in FIG. 11A to FIG. 11G, the device is designed to enable an operator to draw a fluid (e.g., a pharmaceutical liquid or diluent) into the syringe. In this embodiment, mixing syringe housing 20 comprises flange 21 engaged with snap cover 424; and includes mutable proximal chamber 73 prefilled with a diluent or liquid drug 72, and mutable distal chamber 475 into which a liquid drug or other fluid 470 is drawn from an external container (e.g., vial, syringe, drug bag and the like). More specifically, FIG. 11A shows a mixing syringe "as shipped" in which the sterility and integrity of the distal end of syringe housing 22 is protected by cap 23. Distal end 22 is also configured with internal threading 27 for connection with a suitable device for loading and delivering fluid from the syringe. The proximal end of housing 20 also include grip 421. Housing 20 also includes mutable proximal chamber 72 that has been prefilled with liquid substance 73. Distal seal assembly 440 includes the components as detailed in FIG. 10A to FIG. 10C, and the volume of proximal substance 72, i.e., the size of mutable proximal chamber 73, is determined by placement of distal seal assembly 440 and proximal seal 460 within housing 20. The drawing of liquid 470 into the syringe by proximal translation of plunger rod 430, achieved typically by pulling on plunger rod grip 439 (which is connected to plunger rod 430 via a screw/thread connection 438), as shown in FIG. 11B, without causing fluid to be transferred to the proximal chamber 73 is enabled by a locking mechanism (i.e., engagement of plunger protrusions 437, which serve a locking pins within locking groove 451(*a*) in insert 450 in the distal seal assembly as shown in FIG. 10A).

Figure 11C:
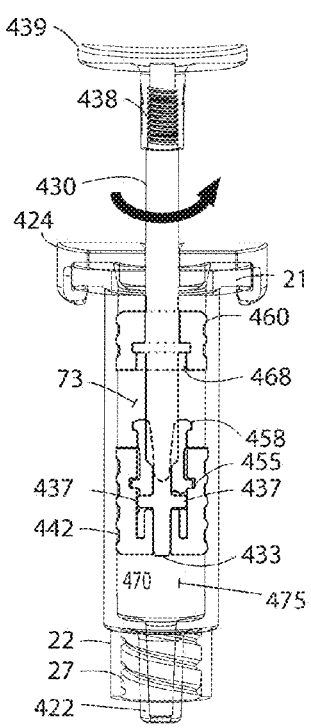
Figures 11D, 11E, 11F, 11G:
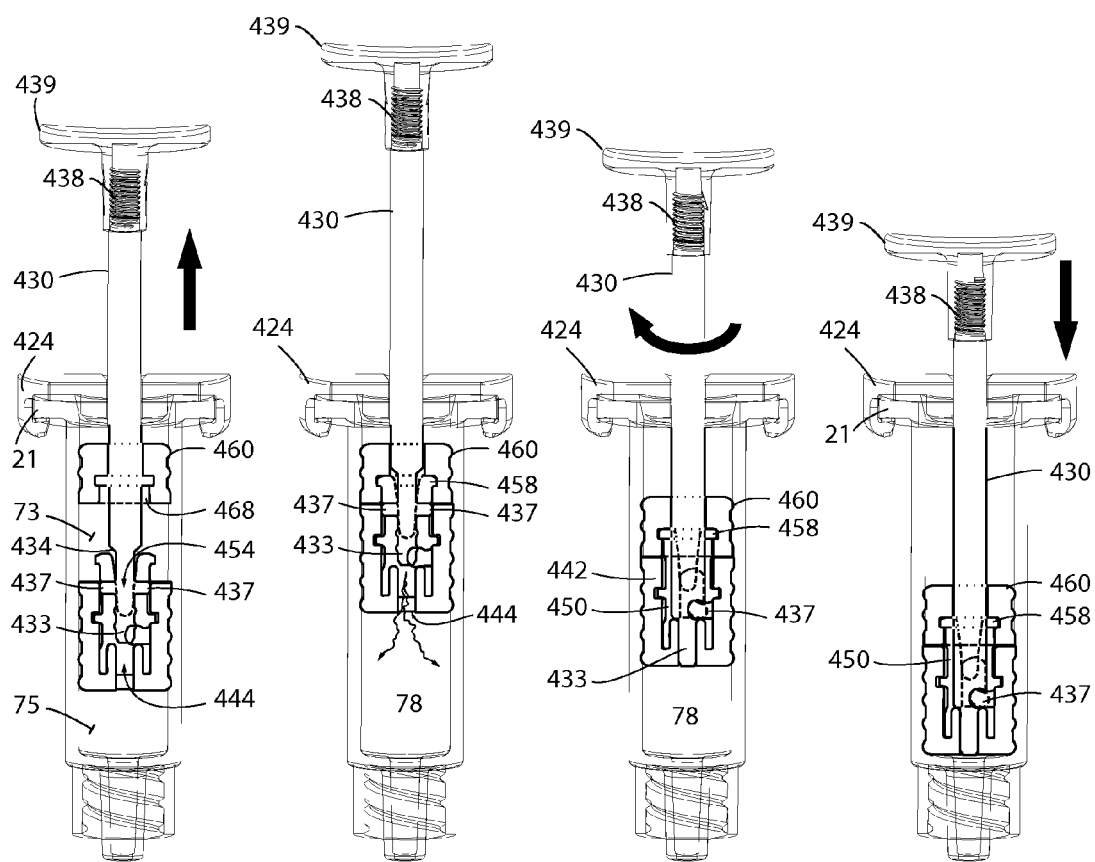

Moreover, the engagement of plunger rod 430 within distal seal assembly 440 allows proximal chamber 73 to substantially maintain its predetermined fill volume and pressure as it is displaced axially, along with proximal seal 460, within housing 20, despite the proximal movement of plunger rod 430. The amount of fluid 470 loaded into the syringe can be exact or approximate; this can be predetermined by the user or by design. This embodiment also provides for optional sequential injection, at least once, from the distal chamber without mixing substances; or in sequential order from mutable distal chamber then mutable proximal chamber. Once liquid 470 has been drawn into mutable chamber 475, by proximal displacement of plunger rod 430 as shown in FIG. 11B, the liquid 470 may be expelled or mixed with proximal substance 72. As shown in FIG. 11C, once distal substance 470 has been drawn into chamber 475, plunger rod 430 can be rotated radially within locking groove 451(*a*) into channel or groove 451 to unlock the valve mechanism (see FIG. 10B). Thereafter, continued proximal displacement of plunger rod 430 until motion is stopped by the interior proximal edge 456 of insert 450 (see FIG. 10C), opening fluid passage 454 and 444 as shown in FIG. 11D.

Because of the engagement of plunger rod 430 with distal seal assembly 440, further proximal displacement of plunger rod 430 causes proximal substance 72 to flow through fluid passages 434, 454 and 444, and mix with distal substance 470 to form mixed substance 478, as mutable proximal chamber 73 shrinks and merges with the expanding mutable distal chamber 475. As shown in FIG. 11E, proximal displacement of distal seal assembly 440 ends with the meeting and connection with proximal seal 460, in which connector 458 is received by complementary connection 468 contained within insert 461 of proximal seal 460. At this stage, mixing is complete, and the mixed substances can be expelled. As shown in FIG. 11F, distal pressure on plunger rod 430, typically by depressing grip 439, pushes plunger rod 430 distally through insert 440 until protrusions 437 are stopped by distal end 457 of channel 451. Optionally, the operator may then radially rotate plunger rod 430 within insert 450 until protrusions 437 abut the interior edge of locking groove 451(*a*) either before or as mixed substance is expelled from distal end of housing 22, as shown in FIG. 11F. Distal pressure on plunger rod 430 by depressing grip 439 ends once substance 478 has been expelled from housing when distal seal assembly abuts the inner distal wall of housing 20, as shown in FIG. 11G.

In another embodiment that provides for sequential injection, a locking aspect that maintains the integrity of the mutable proximal chamber can be configured in a proximal seal assembly. For example, FIG. 12A through FIG. 12D show an embodiment comprising barrel 520 having proximal flange 521, over which is affixed cap 524, typically connected to syringe barrel 520 after fill of at least a proximal substance. This embodiment further includes latch housing 580, which is secured by recess 585 to which plunger rod flange 586 is held by screw/thread connection 538 between plunger rod 530 and plunger button (grip) 539. A portion of plunger rod 530 is further surrounded by seal rod 570, that is secured to the proximal seal by a radial collar 575 gripped within proximal seal interior step 567. Seal rod 570 also includes connectors 578, configured to engage release 581. More specifically, that in the locked position (FIG. 12A and FIG. 12C), release 581 fits into latch housing 580 through a slot, and includes an interior void through which, in the locked position, both the plunger rod and seal rod pass, but into which connector 578 is held in position by ledge 582 and the position of release 581. This locking mechanism configured at the proximal side (surface not contacting the mixing substance) of the proximal seal, coordinates movement of the plunger rod and proximal seal, and because of the tight seal and vacuum forces of the prefilled proximal chamber, proximal translation of the plunger rod, by pulling grip 539, moves the proximal chamber and distal seal assembly in concert with the proximal chamber, and does not dislodge the closed-valve configuration of the distal seal assembly. This configuration ensures concerted motion between the plunger rod and the distal seal assembly when a distal substance is drawn from an external vial/source. As shown in FIG. 12B and FIG. 12D, when the operator is ready to dispense substance from the proximal chamber, or mix the proximal substance with a distal substance, the operator presses interface 583 of release 581 into the slot of latch housing 580, which dislodges ledge 582 from its abutment with rod seal connector 578, freeing plunger rod 530 to move independently of seal rod 570. When this locking feature is disabled, the device operates much the same way as other embodiments described herein (i.e., withdrawing the plunger rod in the proximal direction opens the fluid path to allow mixing). It should be noted that this configuration of the proximal locking mechanism can be adapted for use with any of the distal seal assemblies or valves described herein, without limitation thereto.

Figure 13A:
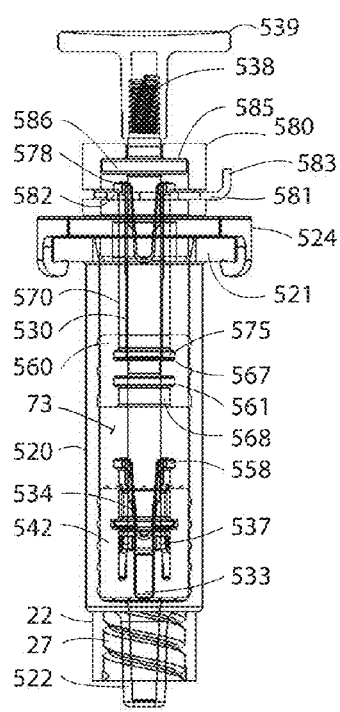
FIG. 13A to FIG. 13G present several views of an embodiment of a syringe in which a locking aspect assembly as shown in FIG. 12 allows the mutable distal chamber to be filled and emptied independent of the prefilled mutable proximal chamber, providing for sequential delivery of substances from the syringe.
Figure 13B:
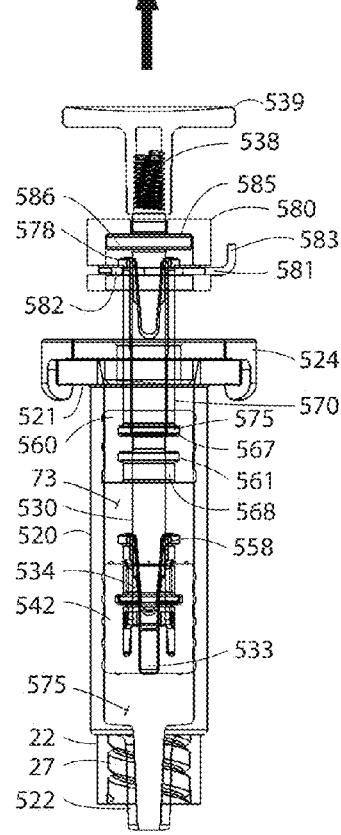

Use of the locking mechanism described with reference to FIG. 12A to FIG. 12D is further illustrated with reference to the particular mixing syringe illustrated in FIG. 13A to FIG. 13G. As shown in FIG. 13A, the mixing syringe comprises barrel housing 20 having distal end 22 and internal threads 27 that can be configured to accept a stopper, luer lock, luer lock adapter, needle assembly, or any suitable connection for capping (as shipped), loading, and delivering the syringe contents (as used). FIG. 13A also shows that this embodiment includes mutable proximal chamber 73 preloaded with substance 72. Substance 72 can be a pharmaceutically active or inactive fluid, adjuvant, diluent, etc., or a mixture of these. The syringe is configured such that the mutable distal chamber can be loaded at or near the time of use. An example of such time-of-use loading is shown in FIG. 13B, in which it is evident that proximal substance 72 in proximal chamber 73 has not been affected by the loading is the distal substance 70 into mutable distal chamber 75. This feature is enabled by the configuration of seal rod 570, which connects proximal seal 560 to plunger rod 530 grip 539 via a latch housing 580 and release 581, as detailed in FIG. 12A and FIG. 12B. Once the syringe components and proximal substance 72 are placed in the syringe, the air-tight, fluid-tight seals formed by proximal seal 560 and distal ring seal 542, the proximal translation of plunger rod 530 is directly translated via seal rod 570 and hub 575 held by step 567 to translation of proximal seal 560, which indirectly causes the distal seal assembly 540 to move in concert in the proximal direction, thereby allowing filling of distal chamber 75 without displacing the valve closure in distal seal assembly 540. Thereafter, the operator can dispense distal substance 70 without mixing substances, which process can be repeated as in FIG. 13A and FIG. 13B as the user requires.

Figure 13C:
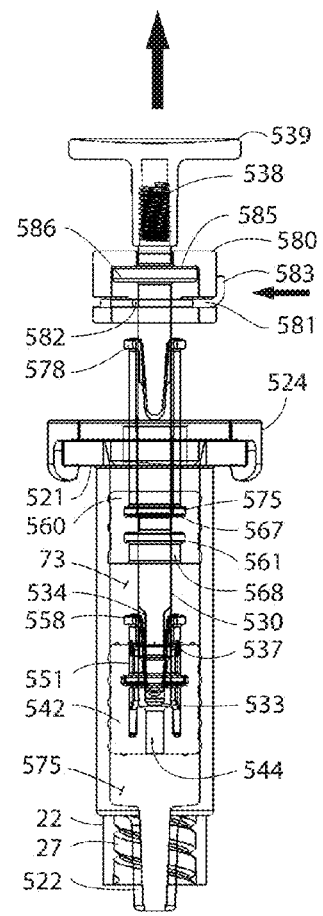
Figures 13D, 13E, 13F, 13G:
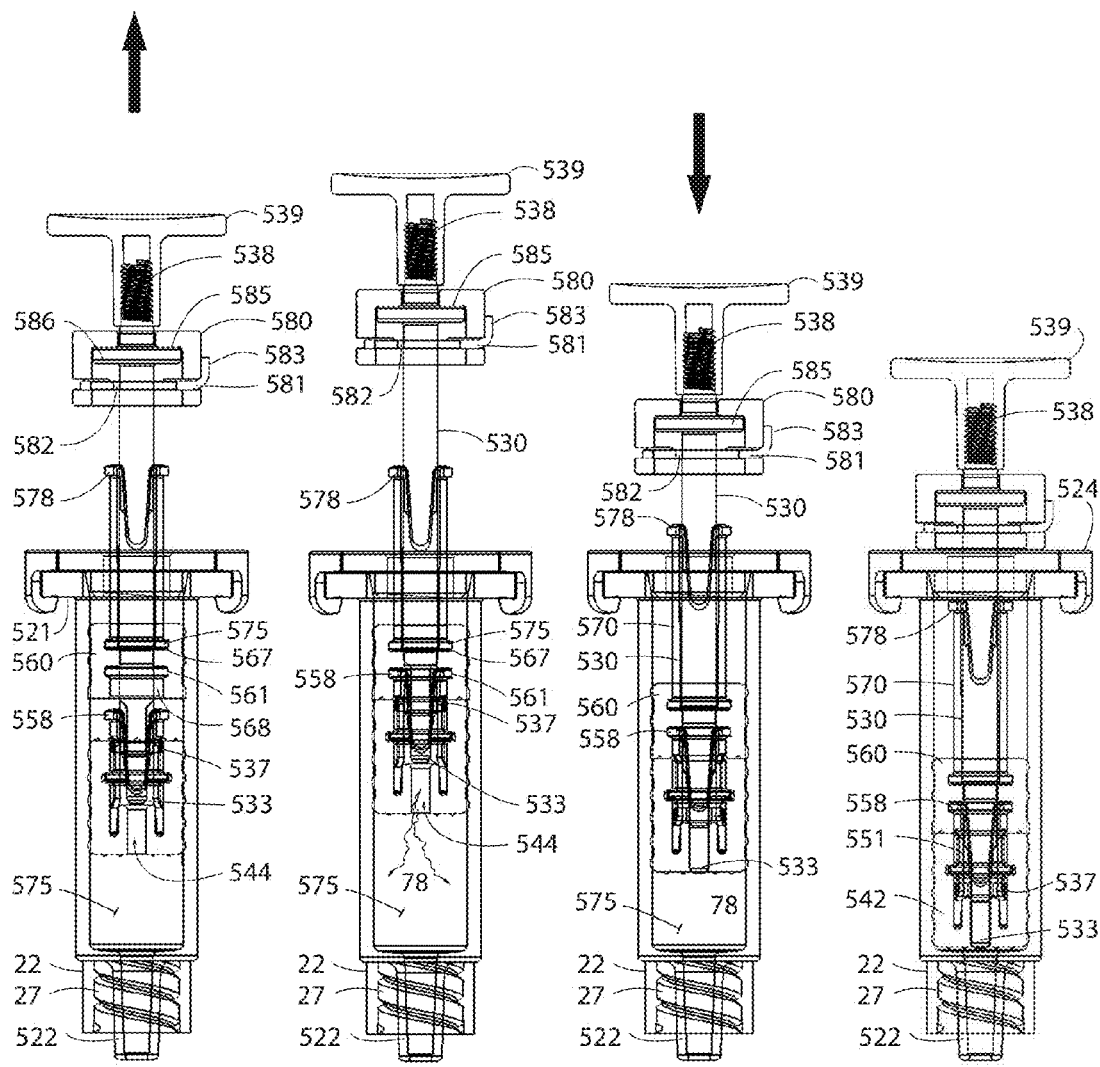

Should the operator desire to mix substances, then distal substance 70 can be drawn into mutable chamber 75 as described, or some portion can be left in mutable distal chamber 75 from prior use, and the valve can be opened. As shown in FIG. 13C, the user pushes interface 583 on release 581, moving it into the slot of latch housing 580, thereby displacing seal rod shoulder 578 from resting place on edge 582, and thus disengaging seal rod 570 from plunger rod 530. As shown in FIG. 13D, then plunger rod 530 is free to dislodge plunger distal end 533 from the closed position in insert 550/distal seal 542 until protrusions 537 abut their distal-most position within channel 551, in other words open the valve and expose channel 534 for fluid passage 544, and proximal substance 72 can flow into distal chamber 75 and mix with substance 70 to form mixed substance 78. The distal seal assembly illustrated in FIG. 13 is similar to that distal seal assembly 340 detailed in FIG. 7, but this valve could have an alternate structure such as distal seal assembly 40, 140, 240 (as detailed in FIG. 6), or another valve structure. As shown in FIG. 13E, further proximal translation of plunger rod 530 displaces proximal substance 72 and collapses mutable proximal chamber 73, until such motion mates connector 558 with recess 568 in insert 561 of proximal seal 560. Thereafter, as shown in FIG. 13F and FIG. 13G, depression of plunger rod 330 closes the valve mechanism, and mixed substance 78 is expelled from the distal end 522 of the mixing syringe.

Optionally, the operator can empty mutable distal chamber 75 (if it had been filled, which is optional in this embodiment), disengage release 581 by pressing 583, then pull on grip 539 to translate rod 530 and open fluid channels 534, 544 and 545 and collapse mutable proximal chamber 73, thereby pushing substance 72 into the portion of the syringe distal to the distal seal (i.e., mutable distal chamber to the extent it exists). This method provides for sole or sequential dispensing of substance 72 without mixing.

As can be seen from the FIG. 10 to FIG. 13 and the preceding discussion, the mixing syringes described herein can be used to dispense mixed substances 78 that have been mixed from prefilled mutable proximal chamber 73 and prefilled mutable distal chamber 75; dispense only distal substance 70; dispense only proximal substance 72 when distal chamber 75 is not filled; dispense distal substance 70, then dispense proximal substance 72; dispense distal substance 70, then dispense mixed substance 78; dispense mixed substances 78 mixed from proximal substance 72, prefilled proximal chamber 73 and fill-at-time-of-use distal substance 70; or practice any other variations of delivery as the configurations of the sequential mixing syringes allow.

Figure 14A:
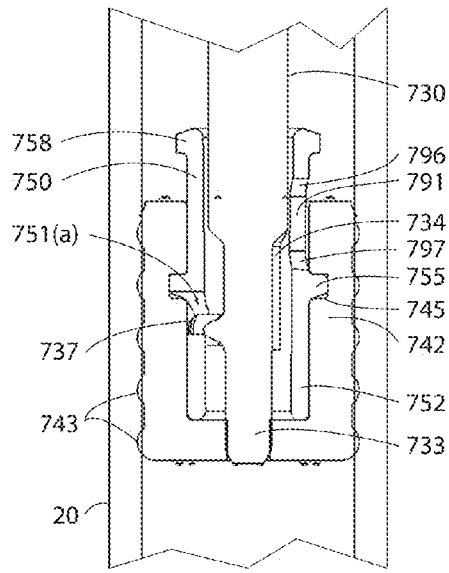
FIG. 14A to FIG. 14 D show several exploded views of various positions of a valve mechanism that allows for repeated mixing and delivery steps from the same mixing syringe.

The embodiments described in FIG. 10 to FIG. 13 may also comprise a connection aspect such as a luer adapter. The connection aspect may be pre-formed as a distal portion of the syringe barrel housing. Alternatively, the syringe barrel may be a substantially straight barrel to which a connection adapter is mounted. An adapter mountable to a syringe barrel may have a luer connection portion and a barrel-engaging portion and a fluid aperture therethrough. The adapter facilitates mounting a luer assembly to the barrel. The luer assembly may be a tip cap having a corresponding female luer fitment for connection to the male luer fitment of the luer connection portion of the adapter. The luer assembly may alternatively be a luer needle assembly having a needle body, cannula, and a needle tip having a corresponding female luer fitment for connection to the male luer fitment of the luer connection portion of the adapter. The term male and female may be used interchangeably to describe corresponding components or aspects thereof. The adapter and syringe further comprise an immobile, compressible needle seal. The needle seal is adjacent to or engageable with the barrel-engaging portion of the adapter. The needle seal sits within the interior of the barrel or adapter, and has a fluid pass-through axially located for the passage of fluid Further embodiments, which can also be used in a variety of methods as just described, provide for mixing syringe devices in which the valve mechanism provides for repetitive mixing steps. An example of a valve embodiment for a repetitive mixing syringe is detailed in FIG. 14A to FIG. 14D. In this embodiment, plunger rod 730 comprises an indentation 734, protrusion (locking pin) 737, and distal end 733. Insert 750 comprises locking groove 751(a) which engages locking pin 737 on plunger rod 730. Insert 750 is held in position within distal seal 742 by hub 752 and radial insert collar 755 which fits into distal seal interior step 745, and distal ring seal 742 is held within barrel 20 by annular ribs 743. FIG. 14A shows plunger rod 730 locked in locking groove 751(a). In this position, distal end 733 of plunger rod 730 blocks passage 744 in distal seal 742, and plunger rod indentation 734 abuts the interior of insert 750 such that fluid passage between the proximal and distal mutable chambers is not possible (i.e., the valve is closed). Insert 750 further comprises channel 751 (not visible in cross section) which allows, when plunger rod 730 is rotated axially and pulled proximally, translation of plunger rod 730 into channel 791.

Figure 14B:
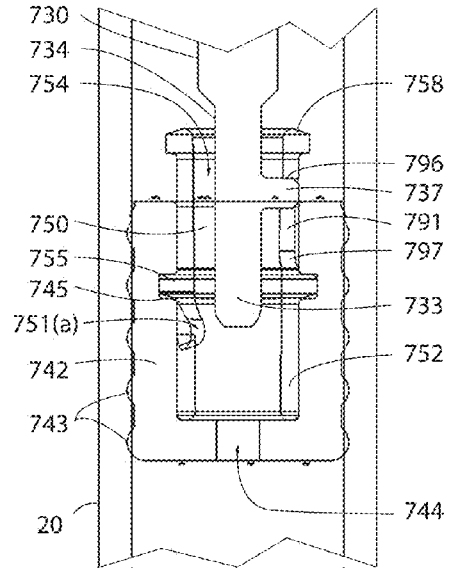
Figure 14C:
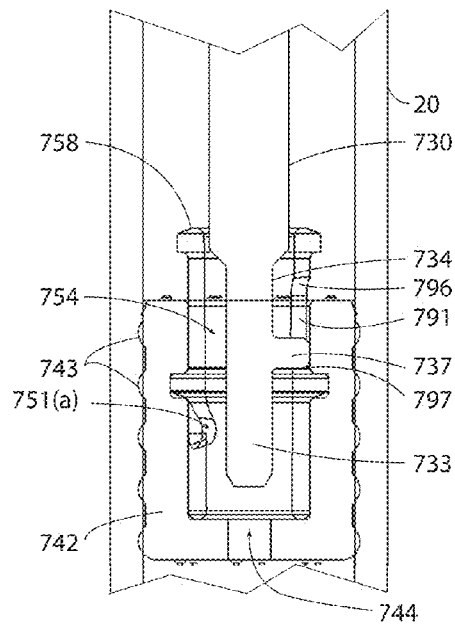
Figure 14D:
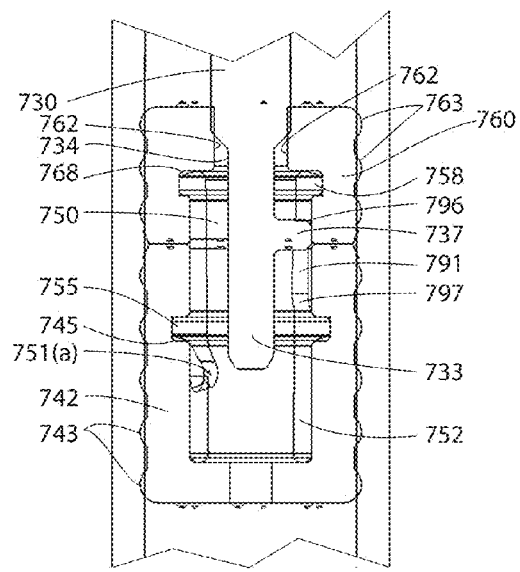

FIG. 14B shows plunger rod 730 in a proximal position within channel 791, in which locking pin 737 is in the distal-most position in channel 791, abutting proximal channel edge 796. Distal and proximal movement of plunger rod 730 is regulated within channel 591 by protrusion 737 which abuts the proximal edge of channel 791 at proximal edge 796, maintaining the engagement of plunger rod 730 and distal seal 742 via insert 750. In the position shown in FIG. 14B, fluid passages 734, 744, and 754 are open, allowing fluid communication between the distal and proximal chambers. FIG. 14C shows plunger rod 730 translated in the distal direction within channel 791 until protrusion 737 abuts edge 797 on the distal edge of channel 791. Plunger rod 730 remains engaged with distal seal 742, via insert 750, and distal seal 742. Moreover, plunger rod 730 is not in the most-distal position within insert 750 (i.e., not in locking groove 751(a)) so that fluid passages are not fully closed in this position. Plunger rod 730 can move within channel 791 between stops 796 and 797, as shown in FIG. 14B and FIG. 14C, until desired mixing is achieved, and translation of the distal seal in this open position allows mixing of proximal and distal substances. This back-and-forth translation can continue until the distal seal assembly has moved to the most-proximal position, as shown in FIG. 14D, in which connector 758 of insert 750 has connected with recess 768 in proximal seal 760. In FIG. 14D, plunger rod 730 abuts interior wall 762 of proximal seal 760, such that no fluid passes proximal seal 760, even though, as shown in FIG. 14D, plunger rod protrusion 737 is in channel 791 and fluid passage remain in the open position. Plunger rod 730 can be translated distally and radially such that protrusion 737 is returned to locking groove 751(a) (as shown in FIG. 14A), such that distal end 733 of plunger rod 730 is fully engaged and blocking fluid passage 744, but the proximal and distal seals remain connected for delivery of the mixed substance (see also FIG. 15F to FIG. 15H).

Figures 15A, 15B, 15C, 15D:
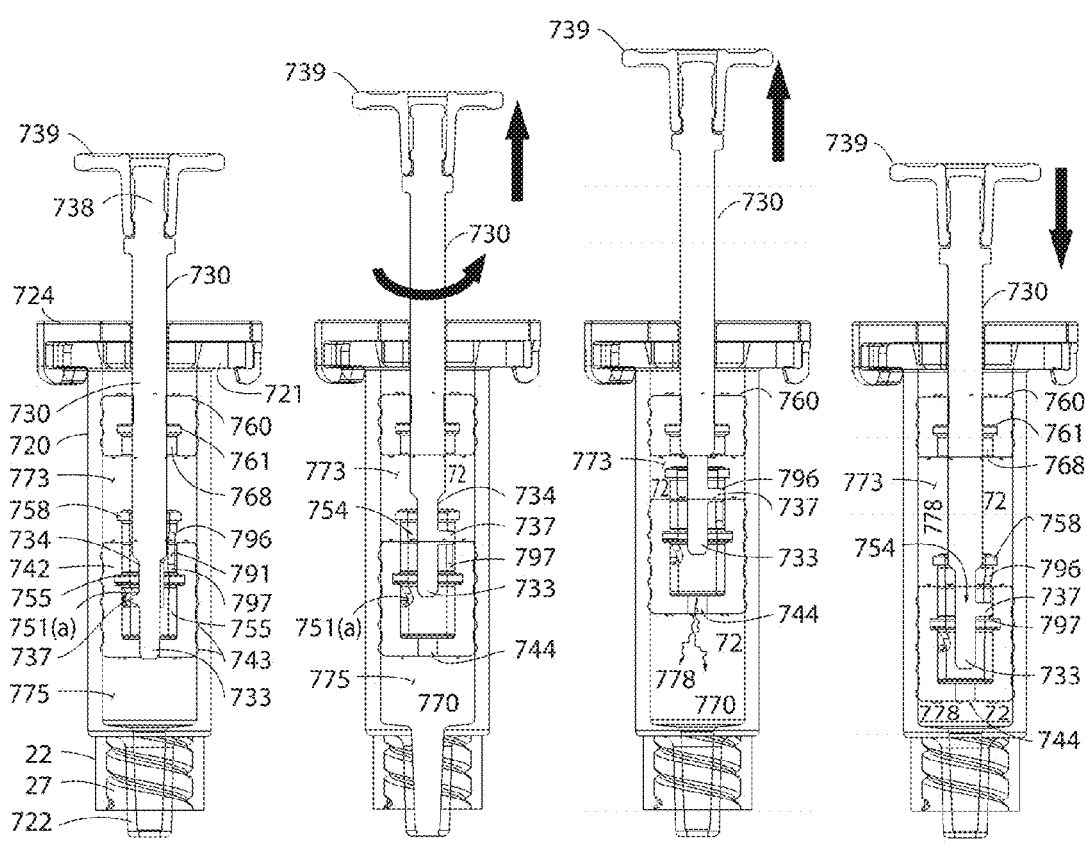
FIG. 15A to FIG. 15H present several views of an embodiment of a mixing syringe in which a valve assembly as shown in FIG. 14 is used to repetitively mix and deliver mixed substances from the syringe.
Figures 15E, 15F, 15G, 15H:
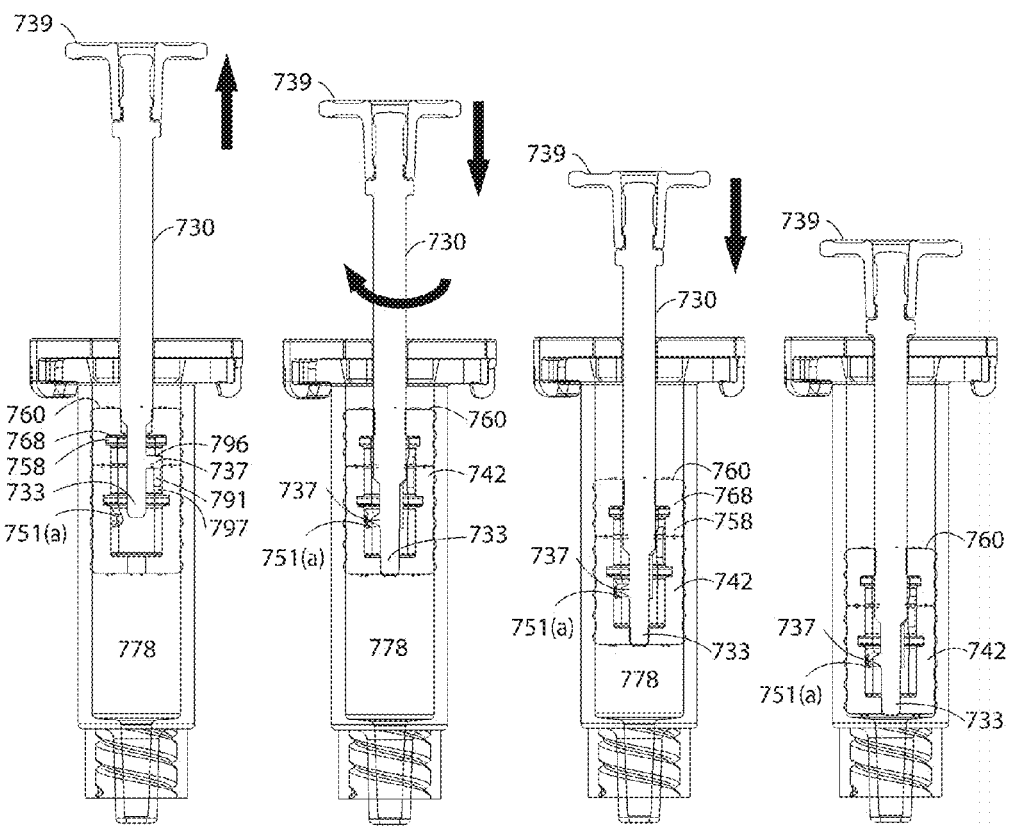

An embodiment of a repetitive mixing syringe is shown in FIG. 15A to FIG. 15H. The mixing syringe includes barrel housing 720 and cap 724 that fits over barrel housing flange 721. In the view shown in FIG. 15A, mutable proximal chamber 773 is prefilled with proximal substance 72 and mutable distal chamber 775 is prefilled with distal substance 70; but this device can also be used when mutable proximal chamber 773 is prefilled with proximal substance 72 and mutable distal chamber is filled at or near time-of-use as described elsewhere herein. This is possible because protrusion 737 serves as a locking pin in locking groove 751(a) such that distal seal 742 can be translated axially without opening passage 744. As shown in FIG. 15B, plunger rod has been moved radially and distally (i.e., pulled and twisted) to the proximal most edge 797 of channel 791. Distal and proximal movement of plunger rod 730 is regulated within channel 591 by locking pin 737 which abuts the proximal edge of channel 791 at proximal edge 796, maintaining the engagement of plunger rod 730 and distal seal 742 via insert 750. As shown in FIG. 15C, because plunger rod 730 remains engaged with distal seal 742, distal seal 742 is moved distally, causing displacement of proximal substance 72 through passage 744. As shown in FIG. 15D, substances can be mixed further by depression of plunger rod 730 within channel 791, such that mixed substance or distal substance is forced proximally through passages 744, 734 and 755. This motion between FIG. 15B, FIG. 15C and FIG. 15D can be repeated as the operator desires. The operator may also use this motion when dispensing the substances (e.g., into an i.v. or needle) for delivery of mixed substances in a gradient from most-distal to most-proximal mixed substances. As shown in FIG. 15E, when the operator pulls plunger rod to the proximal-most position, distal seal 742 meets proximal seal 760 and insert connector 758 connects with recess connection 768 of insert 761, connecting the distal and proximal seal assemblies. Thereafter, as shown in FIG. 15F, plunger rod 730 can be moved distally and radially (i.e., pushed and twisted) such that protrusion 737 locks back in locking groove 751(a) (see FIG. 14A). As shown in FIG. 15G, subsequent distal axial displacement of plunger rod 730, e.g., by pushing button 739 (attached to rod 730 via hub 738), expels mixed substance 778 through the distal end of housing 722. As shown in FIG. 15H, delivery of mixed substance 78 is compete with the distal end of distal seal 742 abuts the interior distal end of housing 20.

In at least one embodiment, the mixing syringe further comprises a retractable needle assembly. An example barrel adapter for retractable needle mechanism is described in WO 2013126118 or PCT/US2014/024781, PCT/US2014/040917, but the mixing syringes as described herein is not limited to that particular configuration. The mixing syringes described herein can be adapted to work with a variety of known retractable needle components, and vice versa. By way of example, the needle safety mechanism may be a needle retraction safety mechanism as described in WO 2006/119570, WO 2006/108243, WO 2009/003234, WO2011/075760, PCT/US2014/024781, PCT/US2014/040917, or U.S. Pat. No. 8,702,653, although without limitation thereto. In at least one embodiment of the present invention, the mixing syringe is also a needle retraction safety syringe and incorporates the needle retraction safety mechanism as disclosed in U.S. Pat. No. 8,702,653, PCT/US2014/024781, or PCT/US2014/040917.

Figure 16A:
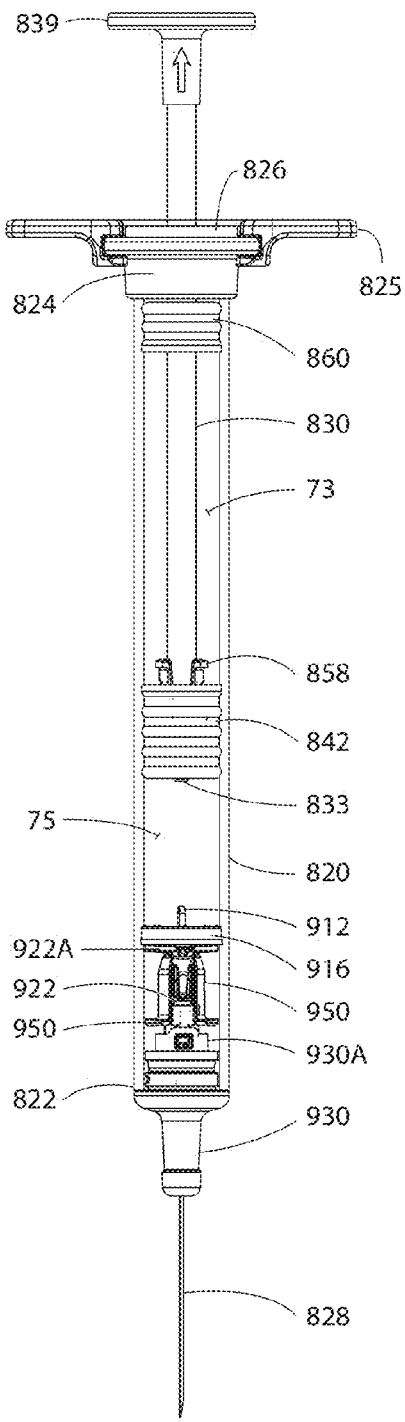
FIG. 16A and FIG. 16B show two views of an embodiment of a mixing syringe that includes an actuation mechanism for needle retraction.
Figure 16B:
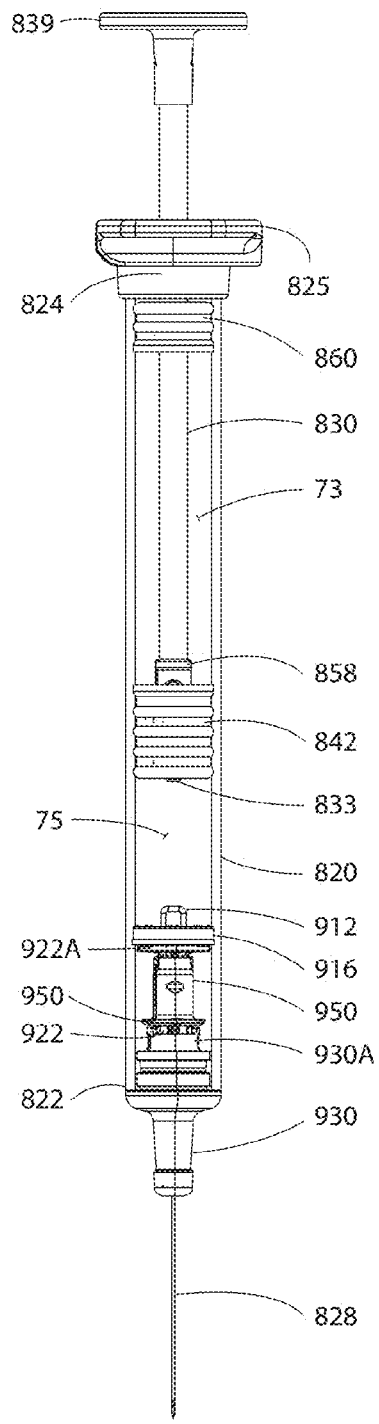

An example embodiment of a mixing syringe further comprising a needle retraction mechanism is shown in FIG. 16A ("front view") and FIG. 16B ("side view"). In the embodiment of FIG. 16A and FIG. 16B, the mixing syringe comprises barrel 820, barrel cover 824 and cap 826 and finger flange 825, which serves as a grip; and within which is axially disposed plunger rod 830 connected on its proximal end to button 839, which also serves as a grip. Plunger rod 830 is engaged with an insert housed within distal ring seal 842, through which the distal-most end 833 of plunger rod 830 protrudes on the distal side, and insert connectors 858 protrude on the proximal side. Insert connectors 858 are configured to mate with a complementary connection in proximal seal 860. The needle retraction mechanism comprises barrel tip 930A, through which needle 828 is visible as the needle cap has been removed for these views. Needle 828 is held in place by needle overmold assembly 922, a portion of which, 922A, abuts a needle seal 916, which seal holds and centers the retractable needle mechanism at the proximal end of needle overmold assembly 922. The distal portion of needle overmold 922 is centered and held in the proximal end of barrel tip 930, in the interior of barrel 820 at distal end 822. Needle overmold 922 is also engaged with snap barrel 950, which is part of the actuator subassembly that permits retraction of the needle. Briefly, snap barrel 950 comprises energized biasing members maintained in energized position by configuration of barrel tip 930 and an engagement of needle overmold assembly 922 and needle seal 916. When mixed substances have been expelled through the needle and the plunger rod presses distally on push bar 912, push bar 912 deforms needle overmold assembly 922 from its position in needle seal 916 such that the proximal end of the actuation mechanism can no longer hold the energized biasing members. As the biasing members spring proximally within barrel, needle 828 is retracted proximally into the barrel. The actuation mechanism can further include a capping or blocking feature that prevents the retracted needle from being exposed, thus protecting the operator and others from accidental needle sticks. In the configuration of FIG. 16, in which the actuation mechanism is inserted into or contiguous with the barrel of the mixing syringe, both the mutable distal chamber and the mutable proximal chamber may be prefilled. Alternatively, a safety needle cartridge or similar device configured for attachment after loading and mixing can be attached via a luer connector, or similar means, to the mixing syringes described herein.

Each of the devices, syringes, components, and methodologies described herein may utilize additional known apparatus, or procedural steps, that are known in the art. Throughout the specification, the aim has been to describe the example embodiments of the invention without limiting the invention to any one embodiment or specific collection of features. Various changes and modifications may be made to the embodiments described and illustrated without departing from the present invention.

The invention claimed is:
1. A prefillable repetitive mixing syringe for administration of at least one substance comprising
   a syringe housing;
   a distal seal assembly axially displaceably disposed within the housing, wherein the position of the distal seal assembly defines a mutable distal chamber and a mutable proximal chamber within the housing;
   the distal seal assembly further comprising a valve that regulates a fluid passage between the proximal and distal chambers;
   a proximal seal;
   a connector configured to connect irreversibly the proximal seal and the distal seal assembly, wherein the connected proximal seal and distal seal assembly translate axially together within the housing; and
   a plunger rod positioned coaxially within the syringe housing and engaged with the distal seal assembly, wherein the plunger rod is configured to releasably engage a locking mechanism to actuate the valve, and whereby the plunger rod can axially displace the distal seal assembly while the fluid passage is open.

2. The repetitive mixing syringe of claim 1, wherein the syringe further comprises an insert housed at least partially within the distal seal assembly, wherein the insert comprises an internal cavity configured to engage a distal end of the plunger rod.

3. The repetitive mixing syringe of claim 2, wherein the insert comprises at least one channel or compartment that regulates movement of the plunger rod within the insert, and wherein the insert comprises at least one fluid passage.

4. The repetitive mixing syringe of claims 2, wherein the insert comprises a connector to irreversibly engage the proximal seal.

5. The repetitive mixing syringe of claim 1, wherein the locking mechanism comprises a radial channel configured to be rotatably engaged by a plunger rod protrusion.

6. The repetitive mixing syringe of claim 1, wherein the distal chamber, proximal chamber, or both, contains a substance.

7. The repetitive mixing syringe of claim 6, wherein the substance comprises a pharmaceutical agent.

8. The repetitive mixing syringe of claim 7, wherein the pharmaceutical agent is selected from the group consisting of a biologic, a vaccine, a chemotherapeutic agent, a contrast agent, a small molecule, an immunogen, an antigen, an interferon, a polyclonal antibody preparation, a monoclonal antibody, an anesthetic, an interfering RNA, a gene vector, an insulin, and a combination of any of these.

9. The repetitive mixing syringe of claim 6, wherein the substance is lyophilized.

10. The repetitive mixing syringe of claim 6, wherein the substance is a diluent.

11. The prefillable repetitive mixing syringe of any one of the preceding claims, wherein the syringe further comprises a dose control mechanism.

12. The prefillable repetitive mixing syringe of claim 1, wherein the syringe further comprises a luer type connection at a distal end of the syringe housing.

13. The prefillable repetitive mixing syringe of claim 1, wherein the mixing syringe further comprises a retractable needle mechanism at a distal end of the syringe housing.

* * * * *